(12) United States Patent
Baras et al.

(10) Patent No.: US 12,315,166 B2
(45) Date of Patent: May 27, 2025

(54) SYSTEMS AND METHODS FOR ANALYZING A STREAM OF IMAGES

(71) Applicant: Given Imaging LTD., Yoqneam (IL)

(72) Inventors: Dorit Baras, Haifa (IL); Eyal Dekel, Haifa (IL); Eva Niv, Hadera (IL)

(73) Assignee: Given Imaging LTD., Yoqneam (IL)

( * ) Notice: Subject to any disclaimer, the term of this patent is extended or adjusted under 35 U.S.C. 154(b) by 431 days.

(21) Appl. No.: 17/916,826

(22) PCT Filed: Apr. 27, 2021

(86) PCT No.: PCT/IL2021/050483
§ 371 (c)(1),
(2) Date: Oct. 4, 2022

(87) PCT Pub. No.: WO2021/220272
PCT Pub. Date: Nov. 4, 2021

(65) Prior Publication Data
US 2023/0148834 A1 May 18, 2023

Related U.S. Application Data

(60) Provisional application No. 63/018,890, filed on May 1, 2020.

(51) Int. Cl.
*A61B 1/00* (2006.01)
*A61B 1/04* (2006.01)
(Continued)

(52) U.S. Cl.
CPC .......... *G06T 7/11* (2017.01); *A61B 1/000094* (2022.02); *A61B 1/000095* (2022.02);
(Continued)

(58) Field of Classification Search
None
See application file for complete search history.

(56) References Cited

U.S. PATENT DOCUMENTS 9,324,145 B1  4/2016  Cherevatsky
11,934,491 B1*  3/2024  Gilinsky ................ G06N 20/00
(Continued)

OTHER PUBLICATIONS

Van Der Putten, Joost et al, "Informative Frame Classification of Endoscopic Videos Using Convolutional Neural Networks and Hidden Markov Models", 2019 IEEE International Conference on Image Processing (ICIP), IEEE Sep. 22, 2019 (Sep. 22, 2019), XP033646924 (3 pages, Abstract).
(Continued)

*Primary Examiner* — Haris Sabah
(74) *Attorney, Agent, or Firm* — Carter, DeLuca & Farrell LLP

(57) ABSTRACT

In accordance with aspects of the present disclosure, a system includes at least one processor and at least one memory storing instructions which, when executed by the processor(s), cause the system to access images of a portion of a gastrointestinal tract (GIT) captured by a capsule endoscopy device; for each of the images, provide, by a deep learning neural network, scores for classifying the image to each of consecutive segments of the GIT; classify each image of a subset of the images, whose scores satisfy a confidence criterion, to one of the consecutive segments of the GIT; refine the classifications of the images in the subset by processing a signal over time corresponding to the classifications of the images in the subset; and estimate, among the images in the subset, a transition (1010) between two adjacent segments of the GIT based on the refined classifications of the images in the subset.

20 Claims, 13 Drawing Sheets

(51) Int. Cl.
  *G06T 7/00* (2017.01)
  *G06T 7/11* (2017.01)
  *G06V 10/25* (2022.01)
  *G06V 10/44* (2022.01)
  *G06V 10/764* (2022.01)
  *G06V 10/82* (2022.01)
  *G06V 30/148* (2022.01)

(52) U.S. Cl.
  CPC ........ *A61B 1/000096* (2022.02); *A61B 1/041* (2013.01); *G06T 7/0012* (2013.01); *G06T 7/97* (2017.01); *G06V 10/25* (2022.01); *G06V 10/454* (2022.01); *G06V 10/764* (2022.01); *G06V 10/82* (2022.01); *G06T 2207/10068* (2013.01); *G06T 2207/20084* (2013.01); *G06T 2207/30028* (2013.01); *G06T 2207/30092* (2013.01); *G06V 30/153* (2022.01); *G06V 2201/031* (2022.01)

(56) References Cited

U.S. PATENT DOCUMENTS

2019/0034800 A1  1/2019  Shiratani
2019/0125173 A1*  5/2019  Lee ..................... G06T 7/0012
2020/0395124 A1*  12/2020  Karlin .................... G16H 30/40
2021/0345865 A1*  11/2021  Spillinger ............. A61B 1/041

OTHER PUBLICATIONS

International Search Report and Written Opinion of the International Searching Authority issued in corresponding application PCT/IL2021/050483 mailed Jul. 30, 2021 (14 pages).

* cited by examiner

SYSTEMS AND METHODS FOR ANALYZING A STREAM OF IMAGES

CROSS-REFERENCE TO RELATED APPLICATIONS

The present application is a U.S. National Stage Application filed under 35 U.S.C. § 371(a) of International Patent Application No. PCT/IL2021/050483, filed Apr. 27, 2021, which claims the benefit of and priority to U.S. Provisional Application No. 63/018,890, filed May 1, 2020, both of which are hereby incorporated by reference herein in their entirety.

FIELD

The disclosure relates to image analysis methods and systems and, more particularly, to systems and methods for analyzing a stream of images based on a change of scenery.

BACKGROUND

Capsule endoscopy (CE) allows examining the entire gastrointestinal tract (GU) endoscopically. There are capsule endoscopy systems and methods that are aimed at examining a specific portion of the GIT, such as the small bowel (SB) or the colon. CE is a non-invasive procedure which does not require the patient to be admitted to a hospital, and the patient can continue most daily activities while the capsule is in his body.

On a typical CE procedure, the patient is referred to a procedure by a physician. The patient then arrives at a medical facility (e.g., a clinic or a hospital), to perform the procedure. The capsule, which is about the size of a multivitamin, is swallowed by the patient under the supervision of a health professional (e.g., a nurse or a physician) at the medical facility and the patient is provided with a wearable device, e.g., a sensor belt and a recorder placed in a pouch and strap to be placed around the patient's shoulder. The wearable device typically includes a storage device. The patient may be given guidance and/or instructions and then released to his daily activities.

The capsule captures images as it travels naturally through the GU. Images and additional data (e.g., metadata) are then transmitted to the recorder that is worn by the patient. The capsule is typically disposable and passes naturally with a bowel movement. The procedure data (e.g., the captured images or a portion of them and additional metadata) is stored on the storage device of the wearable device.

The wearable device is typically returned by the patient to the medical facility with the procedure data stored thereon. The procedure data is then downloaded to a computing device typically located at the medical facility, which has an engine software stored thereon. The received procedure data is then processed by the engine to a compiled study (or "study"). Typically, a study includes thousands of images (around 6,000). Typically, the number of images to be processed is of the order of tens of thousands and about 90,000 on average.

A reader (which may be the procedure supervising physician, a dedicated physician, or the referring physician) may access the study via a reader application. The reader then reviews the study, evaluates the procedure, and provides his input via the reader application. Since the reader needs to review thousands of images, the reading time of a study may usually take between half an hour to an hour on average and the reading task may be tiresome. A report is then generated by the reader application based on the compiled study and the reader's input. On average, it would take an hour to generate a report. The report may include, for example, images of interest, e.g., images which are identified as including pathologies, selected by the reader; evaluation or diagnosis of the patient's medical condition based on the procedure's data (i.e., the study) and/or recommendations for follow up and/or treatment provided by the reader. The report may be then forwarded to the referring physician. The referring physician may decide on a required follow up or treatment based on the report.

SUMMARY

The present disclosure relates to systems and methods for analyzing a stream of images of a gastrointestinal tract (GU). More specifically, the present disclosure relates to determining points in the stream of images corresponding to transitions between particular GU segments, such as transiting between stomach and small bowel, or transitioning between small bowel and colon. Even though examples are shown and described with respect to images captured in vivo by a capsule endoscopy device, the disclosed technology can be applied to images captured by other devices or mechanisms, including anatomical images captured by MRI, for example.

In accordance with aspects of the disclosure, a system for analyzing images includes at least one processor and at least one memory storing instructions. The instructions, when executed by the at least one processor, cause the system to: access a plurality of images of at least a portion of a gastrointestinal tract (GU) captured by a capsule endoscopy device; for each image of the plurality of images, provide, by a deep learning neural network, scores for classifying the image to each of a plurality of consecutive segments of the GU; classify each image of a subset of the plurality of images, whose scores satisfy a confidence criterion, to one of the consecutive segments of the GIT; refine the classifications of the images in the subset by processing a signal over time corresponding to the classifications of the images in the subset; and estimate, among the images in the subset, a transition between two adjacent segments of the consecutive segments of the GIT based on the refined classifications of the images in the subset.

In various embodiments, the instructions, when executed by the at least one processor, further cause the system to provide the subset of the plurality of images as images from the plurality of images whose scores, when normalized, are above an upper threshold or below a lower threshold but are not between the upper threshold and the lower threshold.

In various embodiments, in refining the classifications of the images in the subset, the instructions, when executed by the at least one processor, cause the system to apply a smoothing operation to the classifications of the images in the subset to provide the refined classifications of the images in the subset.

In various embodiments, in applying the smoothing operation, the instructions, when executed by the at least one processor, cause the system to, for each image in the subset: access the classifications of images within a window around the image, and select, as the refined classification of the image, a median of the classifications of the images within the window.

In various embodiments, the transition between the two adjacent segments is a transition between an earlier segment of the GIT and a later segment of the GIT.

In various embodiments, the two adjacent segments are the stomach and the small bowel, and the instructions, when executed by the at least one processor, further cause the system to determine a presence or an absence of a stomach retention condition based on comparing the scores for the plurality of images to a threshold number of small bowel classifications.

In various embodiments, the two adjacent segments include a first segment of the GIT and a second segment of the GIT, and the instructions, when executed by the at least one processor, further cause the system to: for each image of the plurality of images, provide, by a second deep learning neural network, scores for classifying the image to the first segment of the GIT, the second segment of the GIT, and an anatomical feature adjacent to a transition point between the first segment and the second segment; and refine the transition between the first segment and the second segment of the GIT to an earlier point before the estimated transition based on the scores provided by the second deep learning neural network.

In various embodiments, in refining the transition, the instructions, when executed by the at least one processor, cause the system to: (i) for each image of the plurality of images: compute a difference between the score for classifying the image to the first segment of the GIT and the score for classifying the image to the anatomical feature adjacent to the transition point between the first segment and the second segment of the GIT, and compute a sum of the computed differences from a first image of the plurality of images through the image; and (ii) determine the refined transition to be an image corresponding to a global minimum or maximum in the computed sums prior to the originally estimated transition.

In various embodiments, the two adjacent segments include a first segment of the GIT and a second segment of the GIT, and the instructions, when executed by the at least one processor, further cause the system to refine the transition between the first segment and the second segment to a later point after the estimated transition based on at least one of: bursts of classification to the first segment of GIT after the estimated transition, or fluctuation between classification to the first segment of the GIT and classification to the second segment of the GIT, beyond a fluctuation tolerance, after the estimated transition.

In accordance with aspects of the present disclosure, a system for analyzing images includes at least one processor and at least one memory storing instructions. The instructions, when executed by the at least one processor, cause the system to: access a plurality of images of at least a portion of a gastrointestinal tract (GIT) captured by a capsule endoscopy device; estimate, among the plurality of images, a transition between a first segment and a second segment of the GIT based on classification scores from a first deep learning neural network which classifies an image to at least two classifications, where the at least two classifications include the first segment of the GIT and the second segment of the GIT; and refine the transition between the first segment and the second segment of the GIT to an earlier point before the estimated transition based on classification scores for the plurality of images from a second deep learning neural network which classifies an image to at least three classifications, where the at least three classifications include the first segment of the GIT, the second segment of the GIT, and an anatomical feature adjacent to a transition point between the first segment and the second segment of the GIT.

In various embodiments of the system, in refining the transition, the instructions, when executed by the at least one processor, cause the system to: (i) for each image of the plurality of images: compute a difference between the score for classifying the image to the first segment of the GIT and the score for classifying the image to the anatomical feature adjacent to the transition point between the first segment and the second of the GU, and compute a sum of the computed differences from a first image of the plurality of images through the image; and (ii) determine the refined transition to be an image corresponding to a global minimum or maximum in the computed sums prior to the originally estimated transition.

In various embodiments of the system, the first segment of the GU is pre-small bowel, the second segment of the GIT is small bowel, and the anatomical feature adjacent to the transition point between the first segment and the second segment of the GU is a bulb anatomical structure (i.e., the duodenal bulb). In various embodiments of the system, the anatomical feature adjacent to the transition point between the first segment and the second segment of the GU is a pyloric valve.

In accordance with aspects of the present disclosure, a system for analyzing images includes at least one processor and at least one memory storing instructions. The instructions, when executed by the at least one processor, cause the system to: access a plurality of images of at least a portion of a gastrointestinal tract (GIT) captured by a capsule endoscopy device; estimate, among the plurality of images, a first transition between a first segment and a second segment of the GIT based on classification scores from a first deep learning neural network which classifies an image to at least two classifications, where the at least two classifications include the first segment of the GIT and the second segment of the GIT; and refine the transition between the first segment and the second segment of the GU to a later point after the estimate transition based on at least one of: bursts of classification to the first segment of the GU after the estimated transition, or fluctuation between classification to the first segment of the GU and classification to the second segment of the GIT, beyond a fluctuation tolerance, after the estimated transition.

In accordance with aspects of the present disclosure, a system for analyzing images includes at least one processor and at least one memory storing instructions. The instructions, when executed by the at least one processor, cause the system to: access a plurality of images of at least a portion of a gastrointestinal tract (GIT) captured by a capsule endoscopy device; for each image of the plurality of images, provide, by a machine learning system, scores for classifying the image to each of at least two consecutive segments of the GU; perform noise filtering on the classification scores to provide remaining classification scores, where the remaining classification scores correspond to a subset of the plurality of images; classify each image of the subset based on the remaining classification scores to provide a signal corresponding to the classifications; and estimate a transition from an earlier segment to a later segment of the at least two consecutive segments of the GIT based on the classification signal.

In various embodiments of the system, the machine learning system is one of: a deep learning neural network or a classic machine learning system.

In various embodiments of the system, the transition is a transition from pre-small bowel to small bowel, and the instructions are executed in an offline configuration after the capsule endoscopy device has exited a patient. In various embodiments of the system, the instructions, when executed by the at least one processor, cause the system to refine the transition to an earlier transition point corresponding to a global minimum of a function, where the function is based on cumulative sum of differences between classification scores corresponding to the pre-small bowel and classification scores corresponding to an anatomical feature adjacent to a transition point between the pre-small bowel and the small bowel.

In various embodiments of the system, the transition is a transition from small bowel to colon, wherein the instructions are executed in an offline configuration after the capsule endoscopy device has exited a patient. In various embodiments of the system, the instructions, when executed by the at least one processor, cause the system to refine the transition to a later transition point based on at least one of: bursts of classification to the small bowel after the transition, or fluctuation between classification to the small bowel and classification to the colon, beyond a fluctuation tolerance, after the transition.

In various embodiments of the system, the instructions, when executed by the at least one processor, cause the system to remove non-relevant images including at least one of: images occurring before the transition or images occurring after the transition.

In various embodiments of the system, the instructions, when executed by the at least one processor, cause the system to provide localization information to a user, where the localization information includes at least one of: information indicating that images before the transition are classified as images of the earlier segment of the GIT, or information indicating that images after the transition are classified as images of the later segment of the GIT.

In various embodiments of the system, the machine learning system provides scores for classifying images to each of at least three consecutive segments of the GIT, where the transition is a transition from a first segment to a second segment of the at least three consecutive segments of the GIT. The instructions, when executed by the at least one processor, further cause the system to estimate a second transition from the second segment to a third segment of the at least three consecutive segments of the GIT based on the classification signal.

In accordance with aspects of the present disclosure, a system for analyzing images includes: a capsule endoscopy device configured to capture a plurality of images over time of at least a portion of a gastrointestinal tract (GIT) of a person, a receiving device configured to be secured to the person, to be communicatively coupled with the capsule endoscopy device, and to receive the plurality of images; and a computing system configured to be communicatively coupled with the receiving device and to receive the plurality of images, where the computing system includes at least one processor and at least one memory storing instructions. The instructions, when executed by the at least one processor, cause the computing system to: classify each image of the plurality of images, by a machine learning system, to one of at least two consecutive segments of the GIT to provide a classification for each image; estimate occurrence of a transition from an earlier segment to a later segment of the at least two consecutive segments of the GIT based on the classifications for the plurality of images changing from the earlier segment to the later segment and remaining at the later segment for at least one of: a threshold duration or a threshold number of images; and provide a message, based on the estimated occurrence of the transition, that the receiving device can be removed from the person.

In various embodiments of the system, the earlier segment is small bowel and the later segment is colon, and the message indicates that the receiving device can be removed based on the estimated occurrence of the transition from the small bowel to the colon.

In accordance with aspects of the present disclosure, a system for analyzing images includes at least one processor and at least one memory storing instructions. The instructions, when executed by the at least one processor, cause the system to: access, during a capsule endoscopy procedure, a plurality of images captured by a capsule endoscopy device of a portion of a gastrointestinal tract (GIT) traversed by the capsule endoscopy device; for each image of the plurality of images, and during the capsule endoscopy procedure: provide, by a machine learning system, scores for classifying the image to each of at least two consecutive segments of the GIT, and perform an online classification of the image to one of the at least two consecutive segments of the GIT to provide an online classification for the image; provide, during the capsule endoscopy procedure, an online estimated transition from an earlier segment to a later segment of the at least two consecutive segments of the GIT based on causal processing of the online classifications for the plurality of images changing from the earlier segment to the later segment; perform, after the capsule endoscopy procedure ends, an offline classification of each image of a subset of the plurality of images to provide the offline classifications; and provide, after the capsule endoscopy procedure ends, an offline estimated transition from the earlier segment to the later segment of the at least two consecutive segments of the GIT based on non-causal processing of the offline classifications.

In various embodiments of the system, the machine learning system provides scores for classifying images to each of at least three consecutive segments of the GIT, where the offline estimated transition is a transition from a first segment to a second segment of the at least three consecutive segments of the GIT. The instructions, when executed by the at least one processor, further cause the system to estimate a transition from the second segment to a third segment of the at least three consecutive segments of the GIT.

In various embodiments of the system, the instructions, when executed by the at least one processor, cause the system to determine that the capsule endoscopy procedure is at an end based on the online estimated transition.

In accordance with aspects of the present disclosure, a non-transitory machine readable medium stores instructions which, when executed by a processor, cause the processor to perform a method including: classifying each image of a plurality of images, by a machine learning system, to one of at least two consecutive segments of a gastrointestinal tract (GIT) to provide a classification for each image, where the plurality of images are captured over time by a capsule endoscopy device in a person; estimating occurrence of a transition from an earlier segment to a later segment of the at least two consecutive segments of the GIT based on the classifications for the plurality of images changing from the earlier segment to the later segment and remaining at the later segment for at least one of: a threshold duration or a threshold number of images; and providing a message, based on the estimated occurrence of the transition, that a receiving device secured to the person can be removed from the person, where the receiving device is configured to be communicatively coupled with the capsule endoscopy device and to receive the plurality of images.

Further details and aspects of exemplary embodiments of the present disclosure are described in more detail below with reference to the appended figures.

BRIEF DESCRIPTION OF DRAWINGS

The above and other aspects and features of the disclosure will become more apparent in view of the following detailed description when taken in conjunction with the accompanying drawings wherein like reference numerals identify similar or identical elements.

DETAILED DESCRIPTION

The disclosure relates to systems and methods for analyzing medical images and, more particularly, to systems and methods for analyzing a stream of images of a gastrointestinal tract.

The present disclosure provides systems and methods for transition detection in a stream of images captured during a CE procedure. The transition that is detected in the stream of images can be a transition from images of one anatomical area of a gastrointestinal tract (GIT) to images of another, or can be a transition from images of a GIT segment with a pathology present to images of another GIT segment with the pathology not present, or can be a transition from images of a sick/diseased segment to images of a healthy segment, and/or combinations thereof. Accordingly, as used herein, a "segment" of a GIT includes but is not limited to anatomical portions that have given names. Rather, the term "segment" also includes a portion of a GIT having a particular characteristic, such as sick/diseased, healthy, presence of a pathology, and/or absence of a pathology, among other characteristics. Once a transition or transitions are detected, the stream of images can be divided according to the segments of the GIT to which they correspond. Even though examples are shown and described with respect to images captured in vivo by a capsule endoscopy device, the disclosed technology can be applied to images captured by other devices or mechanisms, including anatomical images captured by MRI or images captured with infrared, for example.

In various aspects, the disclosed transition detection utilizes a combination of transition detection operations. Certain transition detection operations are used for detecting a transition from images of pre-small bowel to images of small bowel (e.g., FIGS. 4, 5, 7-10, 12-14), and certain transition detection operations are used for detecting a transition from images of small bowel to images of the colon (e.g., FIGS. 4, 5, 7-10, 15). Additionally, some transition detection operations are suitable for "online" use, i.e., for use at the same time that the capsule progresses through the GIT (e.g., FIGS. 4, 5), while some transition detection operations are suitable for "offline" use, i.e., after the capsule has exited the patient body (e.g., FIGS. 4, 5, 7-10, 12-15).

Figure 4:
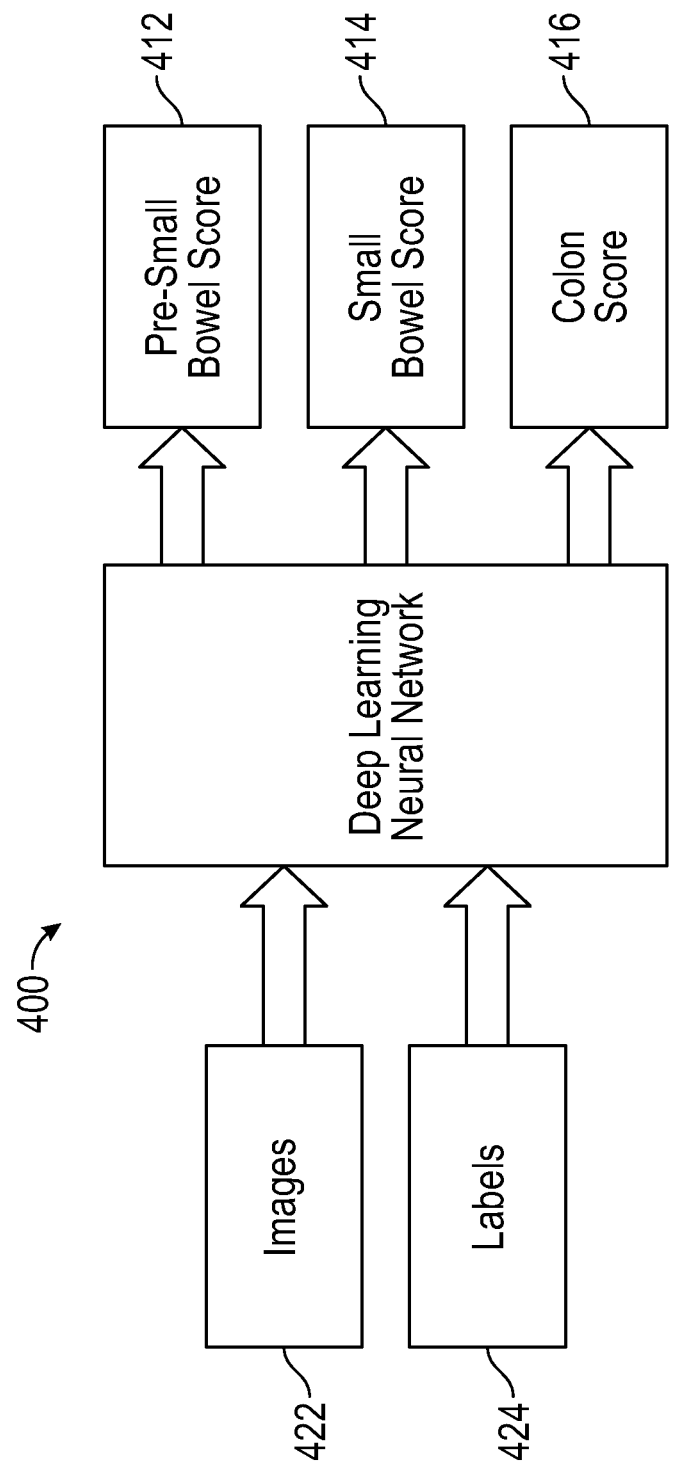
FIG. 4 is a block diagram of an exemplary deep learning neural network, in accordance with aspects of the disclosure.
Figure 5:
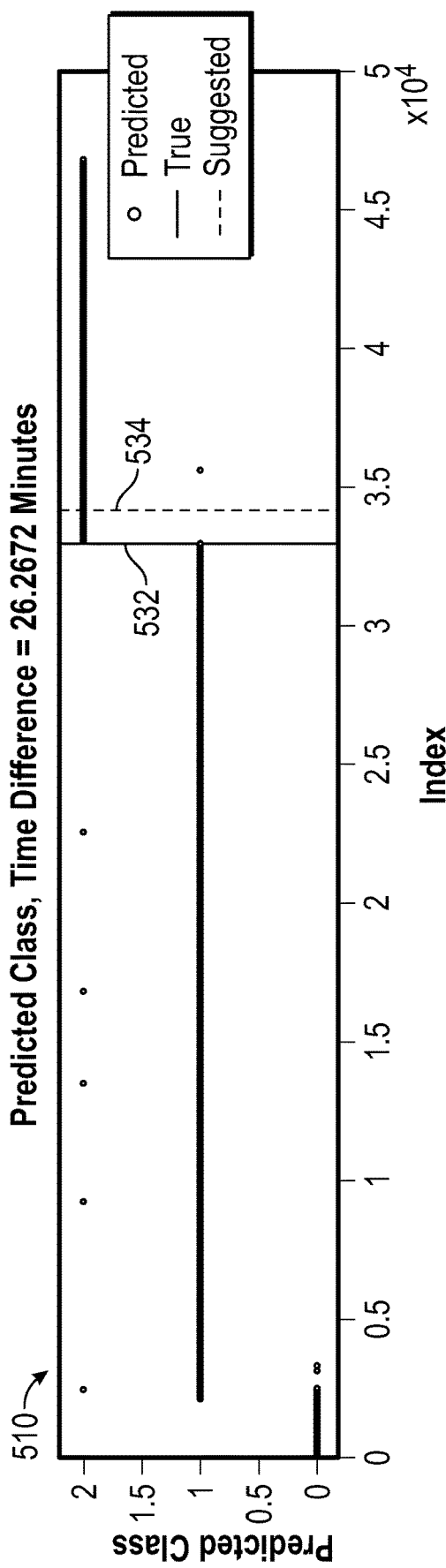
FIG. 5 is a graph of exemplary classification scores and predicted classes based on the deep learning neural network of FIG. 4, in accordance with aspects of the disclosure.
Figure 5:
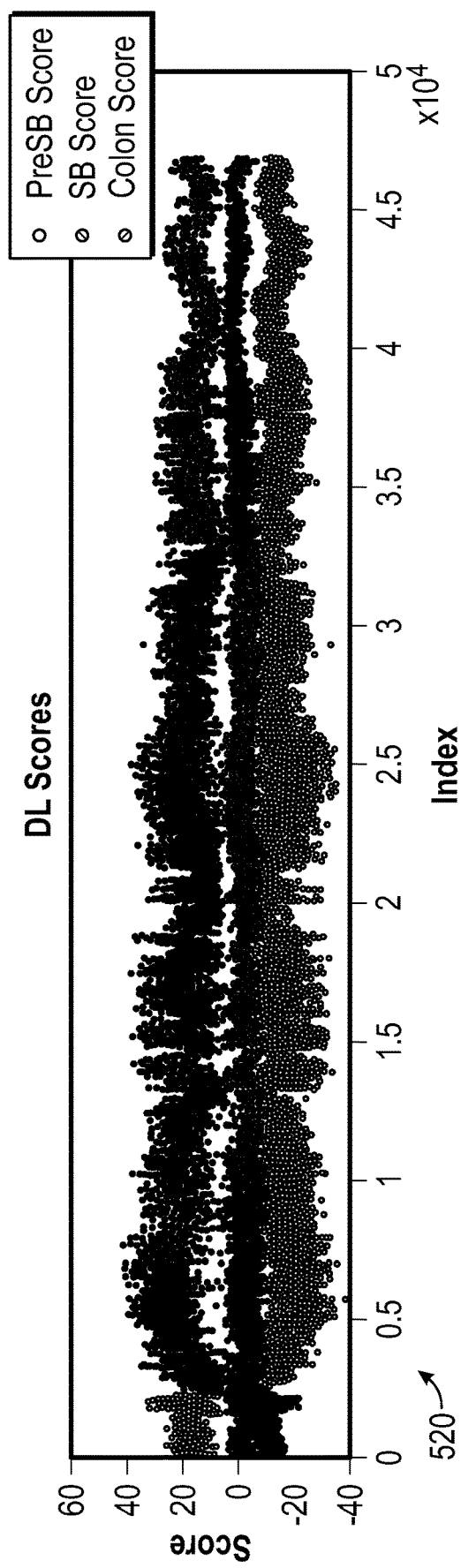
Figure 12:
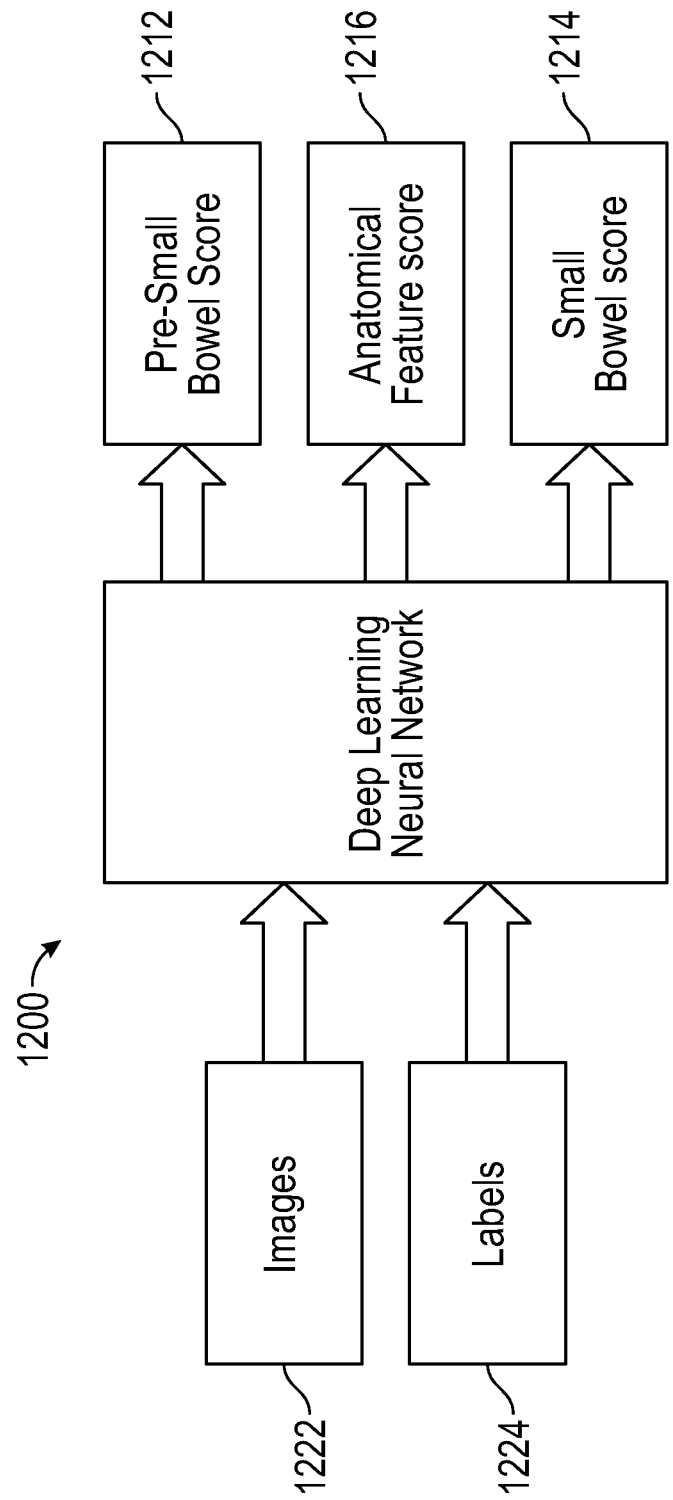
FIG. 12 is a block diagram of another exemplary deep learning neural network, in accordance with aspects of the disclosure.
Figure 13:
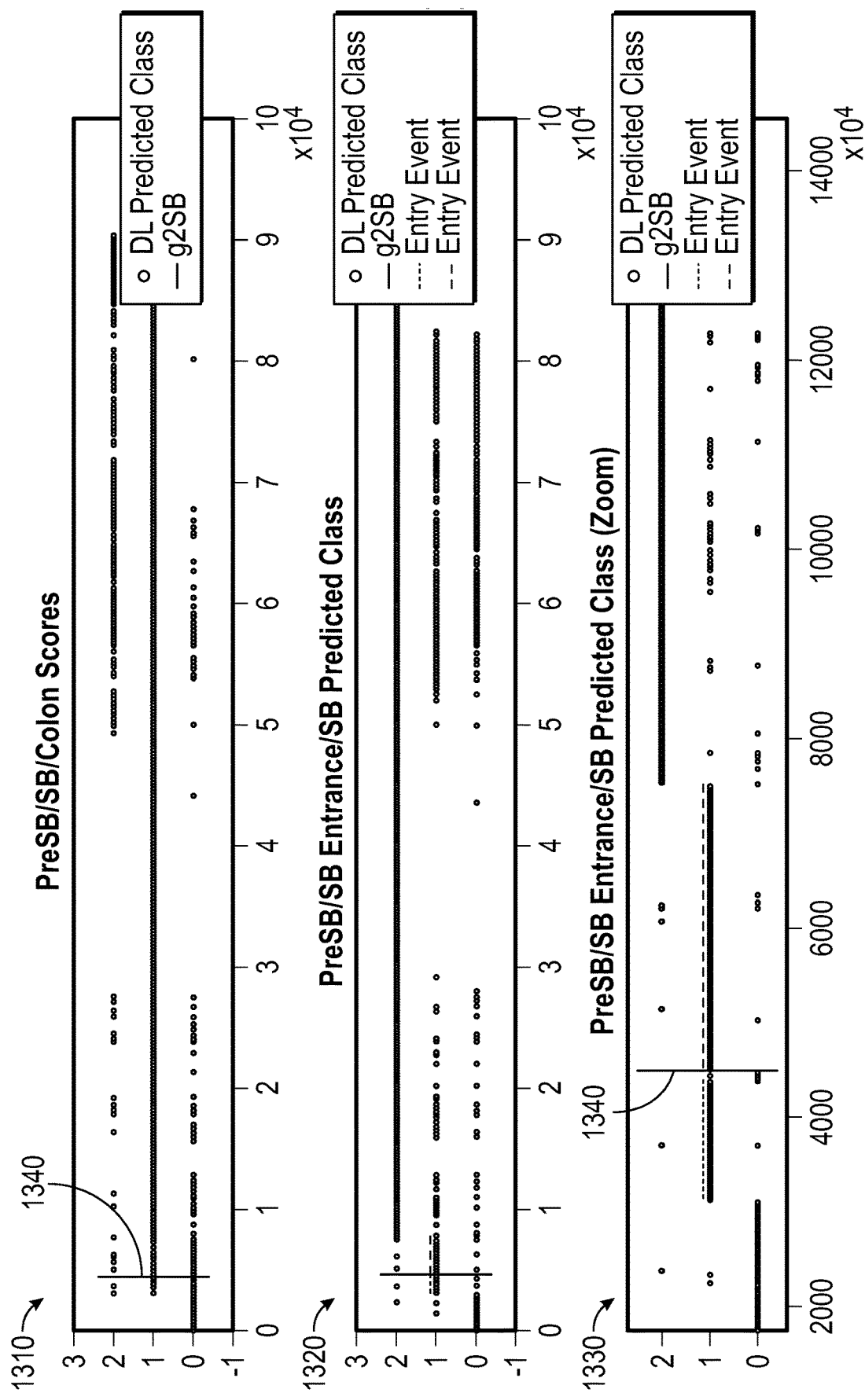
FIG. 13 is a graph of exemplary classifications provided by the deep learning neural networks of FIGS. 4 and 12, in accordance with aspects of the disclosure.
Figure 14:
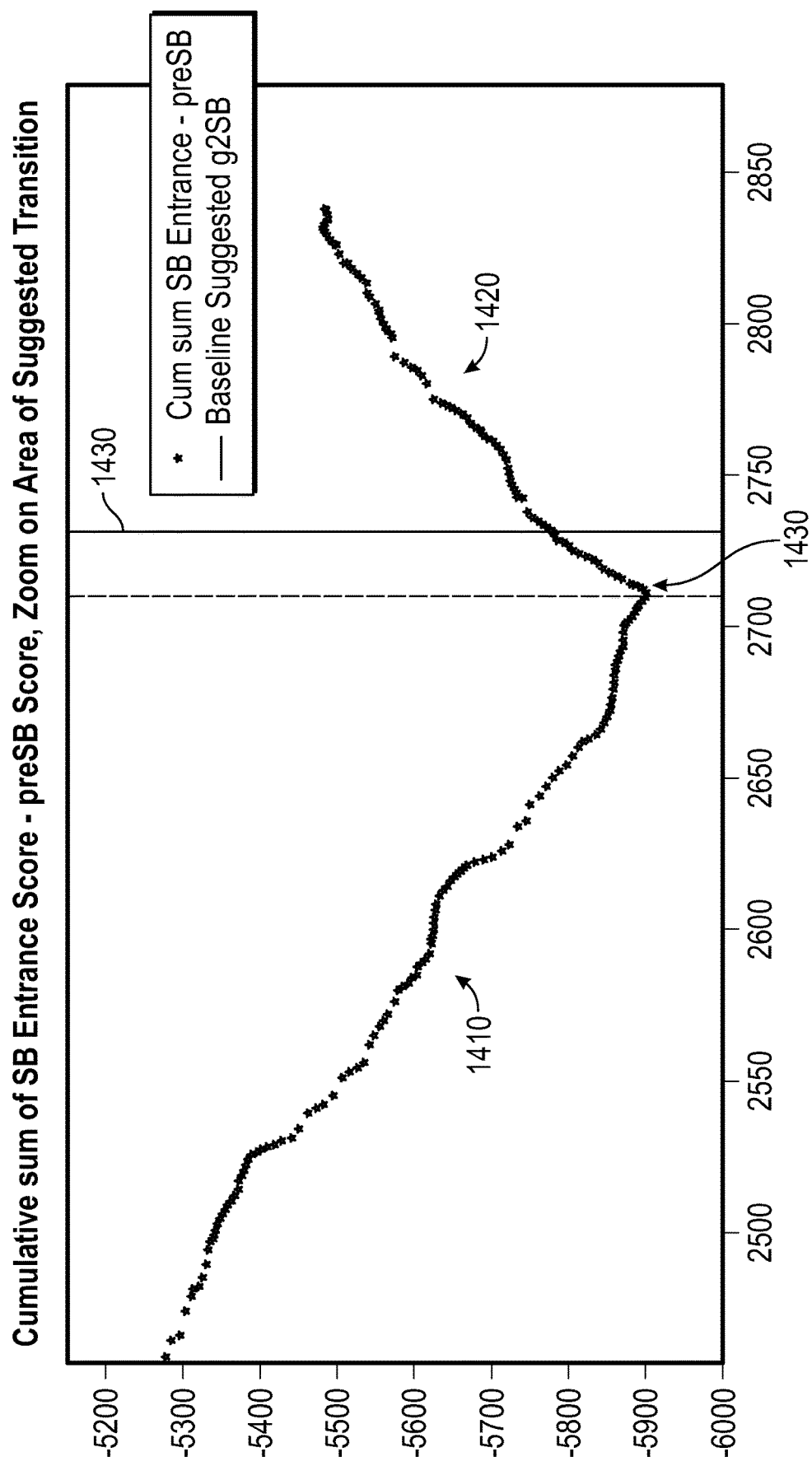
FIG. 14 is a graph of exemplary values computed based on the classification scores provided by the deep learning neural network of FIG. 12.
Figure 15:
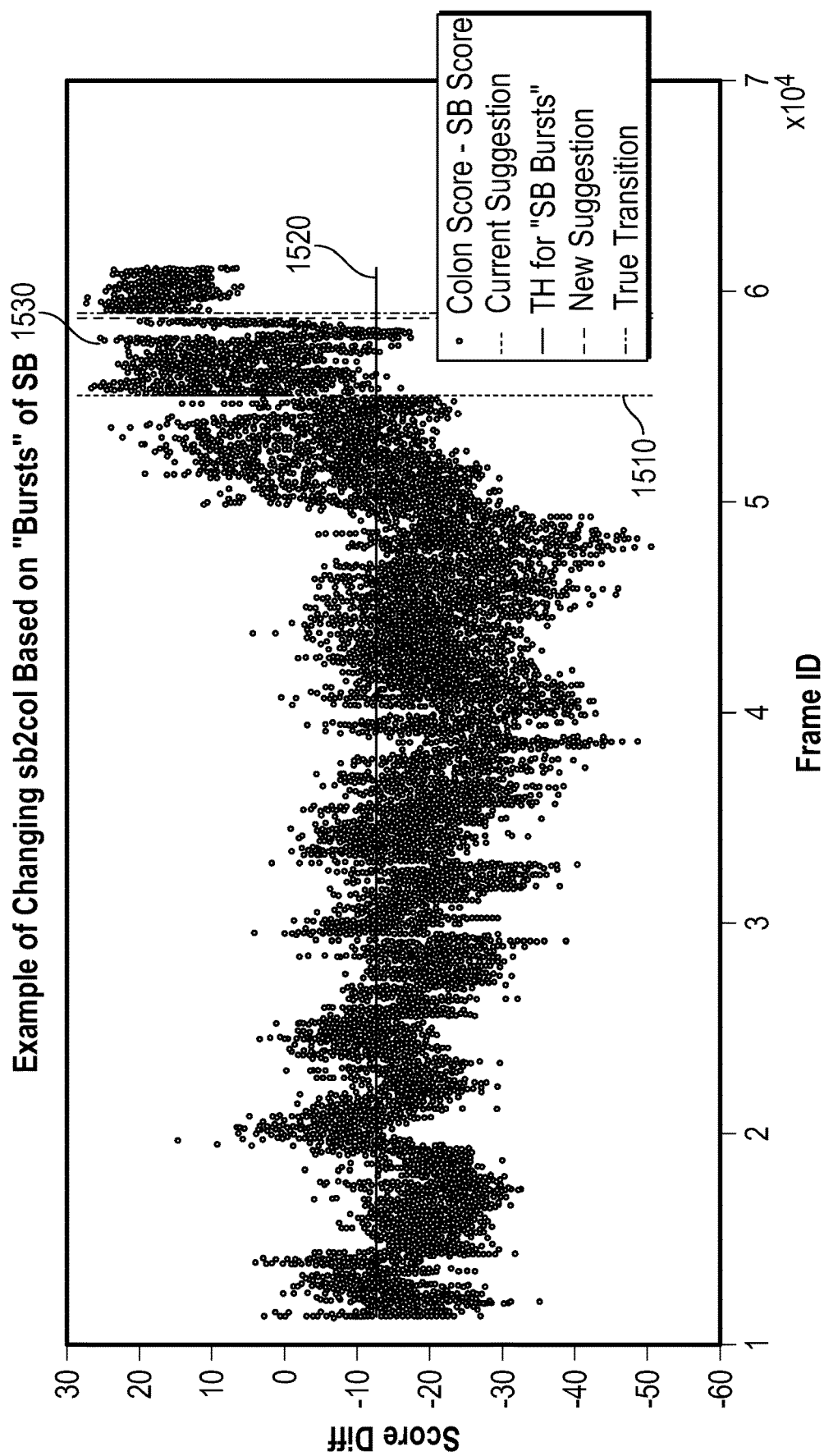
FIG. 15 is a graph of exemplary classification scores exhibiting bursts of classifications after an estimated transition, in accordance with aspects of the disclosure.

As a brief summary, the transition detection operations of FIGS. 4 and 5 are usable for both online and offline transition detection. The operations of FIGS. 7-10 and 12-15 are mainly contemplated for offline transition detection, but depending on availability of computing resources, some or all aspects of such figures may be applicable for online transition detection as well. The detection operations of FIGS. 4, 5, and 7-10 are usable for detecting transitions between multiple segments of the GIT, such as detecting a transition from images of pre-small bowel to images of small bowel, as well as detecting a transition from images of small bowel to images of the colon. The operations of FIGS. 12-14 are mainly contemplated for detecting a transition from images of pre-small bowel to images of small bowel, and the operations of FIG. 15 are mainly contemplated for detecting a transition from images of small bowel to images of the colon. However, the operations of FIGS. 12-15 can be adapted and applied to detection of other transitions as well.

As another way of summarizing aspects of the present disclosure, online detection of transition between images of pre-small bowel and images of the small bowel, and/or transition between images of small bowel and images of the colon, can apply the operations of FIGS. 4 and 5. Offline detection of transition between images of pre-small bowel and images of small bowel can apply some or all operations of FIGS. 4, 5, 7-10, and 12-14. Offline detection of transition between images of small bowel and images of the colon can apply some or all operations of FIGS. 4, 5, 7-10, and 15. Depending on availability of computing resources, online detection of transitions may apply some or all operations of FIGS. 7-10 and 12-15.

By detecting transitions in a stream of in-vivo images, in accordance with the present disclosure, portions of the stream of images can be identified to provide localization information to the reader of a study (typically a physician) and/or to remove images which are not relevant. According to some aspects of the present disclosure, a user (e.g., a physician), may build his or her understanding of a case by reviewing a study, which includes a display of images (e.g., captured by the CE imaging device 212) that were selected, e.g., automatically, as images that may be of interest. Since the study typically includes thousands of images, its review may be a tiresome task. Reducing the number of images included in a study may ease the review process for the user, reduce the reading time per case and may lead to better diagnosis. For example, in a small bowel procedure, once the transition to the colon is identified, all the images captured after the transition point may be removed. This may facilitate the generation of a study having a reduced number of images and thus may reduce the study reading time. Furthermore, it may save processing time and resources.

In various embodiments, transition detection can be utilized online to indicate the end of a procedure, which would "release" the patient and allow the patient to be uncoupled from equipment while the capsule progresses through non-relevant portions of the GIT. In various embodiments, transition detection can be used to define an anatomical area of interest (e.g., the small bowel) and/or to segment the GIT (or a portion of it) into different anatomical areas. Various combinations of one or more such embodiments are contemplated to be within the scope of the present disclosure.

In the following detailed description, specific details are set forth in order to provide a thorough understanding of the disclosure. However, it will be understood by those skilled in the art that the disclosure may be practiced without these specific details. In other instances, well-known methods, procedures, and components have not been described in detail so as not to obscure the present disclosure. Some features or elements described with respect to one system may be combined with features or elements described with respect to other systems. For the sake of clarity, discussion of same or similar features or elements may not be repeated.

Although the disclosure is not limited in this regard, discussions utilizing terms such as, for example, "processing," "computing," "calculating," "determining," "establishing," "analyzing," "checking," or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although the disclosure is not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the methods described herein are not constrained to a particular order or sequence. Additionally, some of the described methods or elements thereof can occur or be performed simultaneously, at the same point in time, or concurrently.

The term "location" and its derivatives, as referred to herein with respect to an image, may refer to the estimated location of the capsule along the GU while capturing the image or to the estimated location of the portion of the GIT shown in the image along the GU.

A type of CE procedure may be determined based on, inter alia, the portion of the GIT that is of interest and is to be imaged (e.g., the colon or the small bowel ("SB")), or based on the specific use (e.g., for checking the status of a GI disease, such as Crohn's disease, or for colon cancer screening).

The terms "surrounding" or "adjacent" as referred to herein with respect to images (e.g., images that surround another image(s), or that are adjacent to other image(s)), may relate to spatial and/or temporal characteristics unless specifically indicated otherwise. For example, images that surround or are adjacent to other image(s) may be images that are estimated to be located near the other image(s) along the GIT and/or images that were captured near the capture time of another image, within a certain threshold, e.g., within one or two centimeters, or within one, five, or ten seconds.

The terms "GU" and "a portion of the GIT" may each refer to or include the other, according to their context. Thus, the term "a portion of the GIT" may also refer to the entire GIT and the term "GU" may also refer only to a portion of the GU.

The terms "image" and "frame" may each refer to or include the other and may be used interchangeably in the present disclosure to refer to a single capture by an imaging device. For convenience, the term "image" may be used more frequently in the present disclosure, but it will be understood that references to an image shall apply to a frame as well.

The term "classification score(s)" or "score(s)" may be used throughout the specification to indicate a value or a vector of values for a category or a set of categories applicable to an image/frame. In various implementations, the value or vector of values of a classification score or classification scores may be or may reflect probabilities. In various embodiments, a model may output classification scores which may be probabilities. In various embodiments, a model may output classification scores which may not be probabilities.

As used herein, a "machine learning system" means and includes any computing system that implements any type of machine learning. As used herein, "deep learning neural network" refers to and includes a neural network having several hidden layers and which does not require feature selection or feature engineering. A "classical" machine learning system, in contrast, is a machine learning system which requires feature selection or feature engineering.

Figure 1:
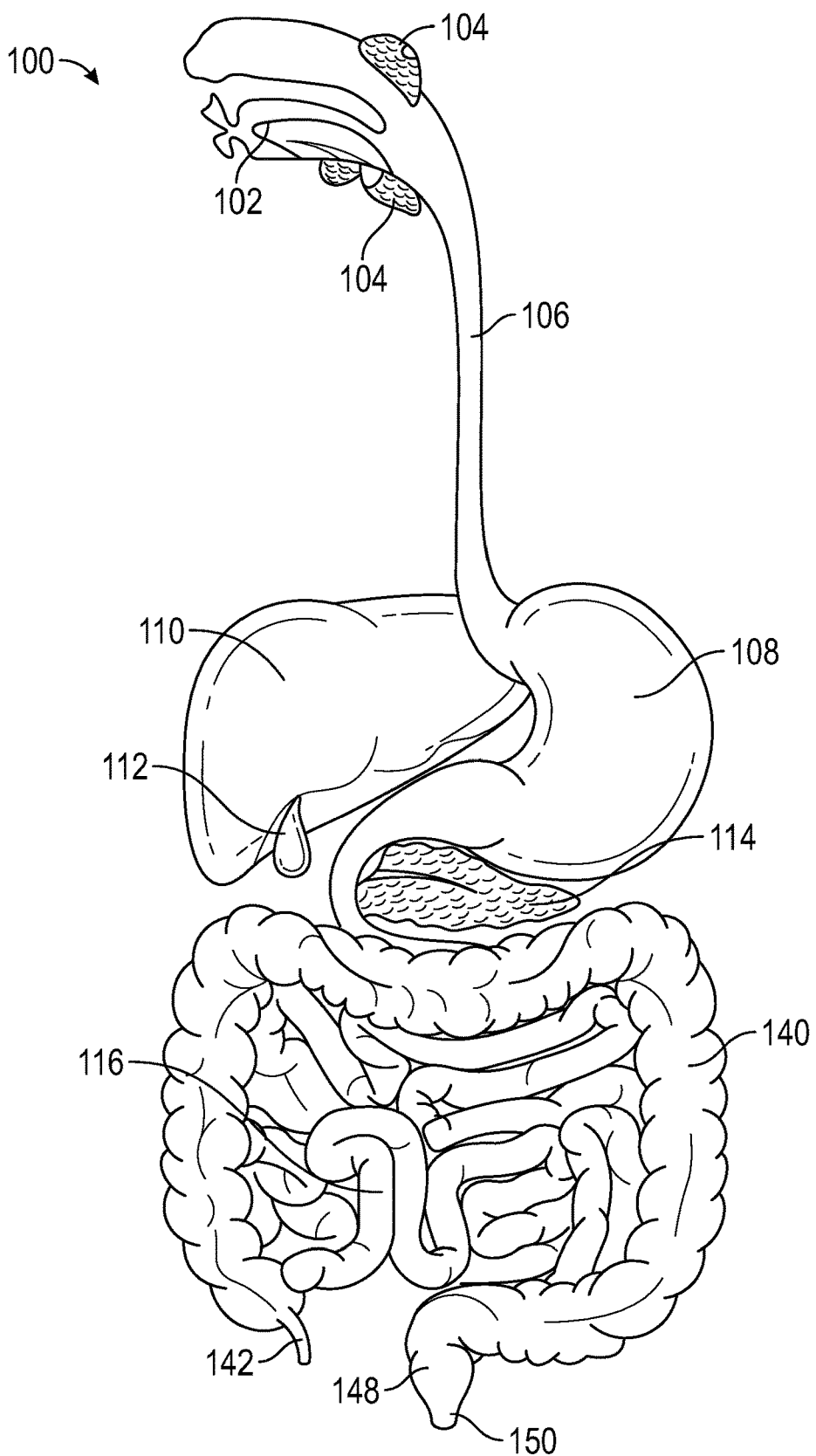
FIG. 1 is a diagram illustrating a gastrointestinal tract (GIT), in accordance with aspects of the disclosure.

Referring to FIG. 1, an illustration of the GU 100 is shown. The GU 100 is an organ system within humans and other animals. The GIT 100 generally includes a mouth 102 for taking in sustenance, salivary glands 104 for producing saliva, an esophagus 106 through which food passes aided by contractions, a stomach 108 to secrete acid to aid in digesting food, a liver 110, a gall bladder 112, a pancreas 114, a small intestine 116 (e.g., SB) for the absorption of nutrients, and a colon 400 (e.g., large intestine) for the absorption of water and storage of waste material as feces prior to defecation. Food taken in through the mouth is digested by the GIT to take in nutrients and the remaining waste is expelled as feces through the anus 430.

Studies of different portions of the GIT 100 (e.g., SB), colon 400, esophagus 106, and/or stomach 108 may be presented via a suitable user interface. As used herein, the terms "study" and "studies" refer to and include at least a set of images selected from the images captured by a CE imaging device (e.g., 212, FIG. 2) and can optionally include information other than images as well. The type of procedure performed may determine which portion of the GU 100 is the portion of interest. Examples of types of procedures performed include, without limitation, an SB procedure, a colon procedure, an SB and colon procedure, a procedure aimed to specifically exhibit or check the SB, a procedure aimed to specifically exhibit or check the colon, a procedure aimed to specifically exhibit or check the colon and the SB, or a procedure to exhibit or check the entire GIT: esophagus, stomach, SB, and colon.

Figure 2:
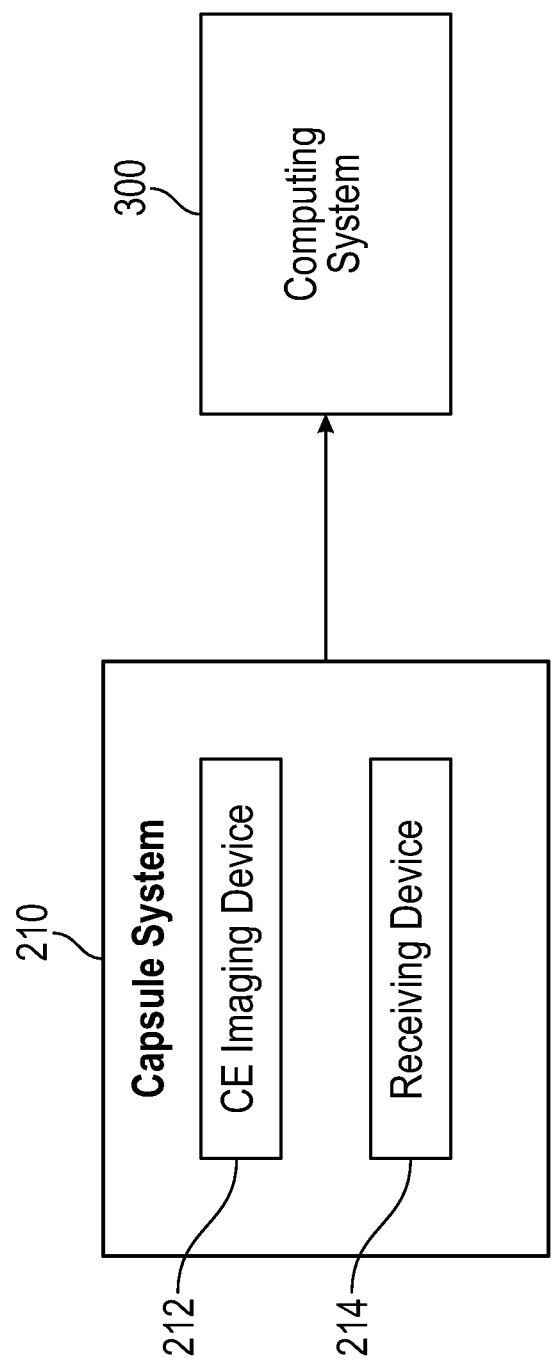
FIG. 2 is a block diagram of an exemplary system for analyzing images captured in vivo by a capsule endoscopy device, in accordance with aspects of the disclosure.

FIG. 2 shows a block diagram of a system for analyzing medical images captured in vivo via a CE procedure. The system generally includes a capsule system 210 configured to capture images of the GU and a computing system 300 (e.g., local system and/or cloud system) configured to process the captured images.

The capsule system 210 may include a swallowable CE imaging device 212 (e.g., a capsule) configured to capture images of the GIT as the CE imaging device 212 travels through the GIT. The images may be stored on the CE imaging device 212 and/or transmitted to a receiving device 214 typically including an antenna. In some capsule systems 210, the receiving device 214 may be located on the patient who swallowed the CE imaging device 212 and may, for example, take the form of a belt worn by the patient or a patch secured to the patient.

The capsule system 210 may be communicatively coupled with the computing system 300 and can communicate captured images to the computing system 300. The computing system 300 may process the received images using image processing technologies, machine learning technologies, and/or signal processing technologies, among other technologies. The computing system 300 can include local computing devices that are local to the patient and/or the patient's treatment facility, a cloud computing platform that is provided by cloud services, or a combination of local computing devices and a cloud computing platform.

In the case where the computing system 300 includes a cloud computing platform, the images captured by the capsule system 210 may be transmitted online to the cloud computing platform. In various embodiments, the images can be transmitted via the receiving device 214 worn or carried by the patient. In various embodiments, the images can be transmitted via the patient's smartphone or via any other device connected to the Internet and which may be coupled with the CE imaging device 212 or the receiving device 214.

Figure 3:
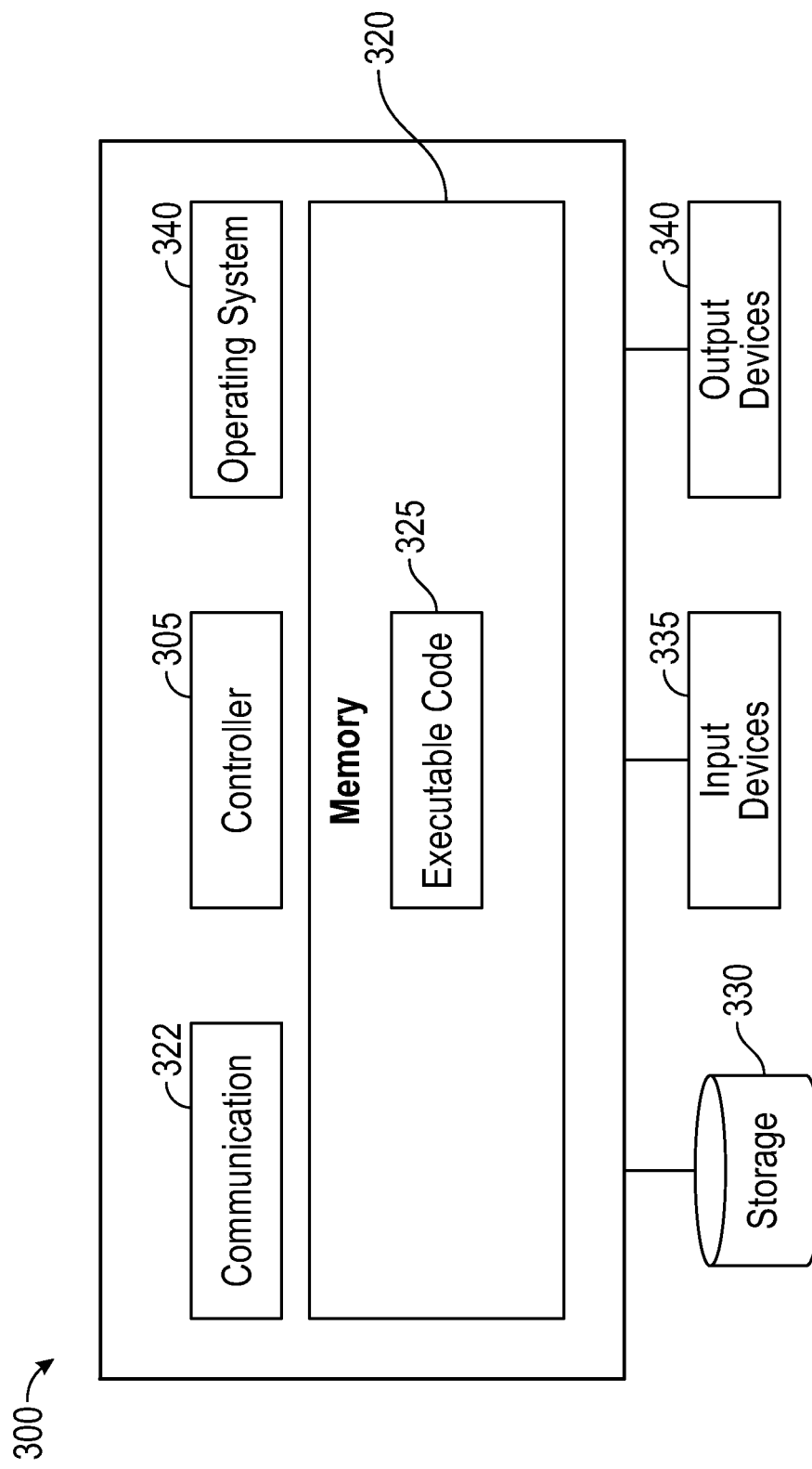
FIG. 3 is a block diagram of an exemplary computing device, in accordance with aspects of the disclosure.

FIG. 3 shows a high-level block diagram of an exemplary computing system 300 that may be used with image analyzing systems of the present disclosure. Computing system 300 may include a processor or controller 305 that may be or include, for example, one or more central processing unit processor(s) (CPU), one or more Graphics Processing Unit(s) (GPU or GPGPU), a chip or any suitable computing or computational device, an operating system 215, a memory 320, a storage 330, input devices 335 and output devices 340. Modules or equipment for collecting or receiving (e.g., a receiver worn on a patient) or displaying or selecting for display (e.g., a workstation) medical images collected by the CE imaging device 212 (FIG. 2) may be or include, or may be executed by, the computing system 300 shown in FIG. 3. A communication component 322 of the computing system 300 may allow communications with remote or external devices, e.g., via the Internet or another network, via radio, or via a suitable network protocol such as File Transfer Protocol (FTP), etc.

The computing system 300 includes an operating system 315 that may be or may include any code segment designed and/or configured to perform tasks involving coordination, scheduling, arbitration, supervising, controlling or otherwise managing operation of computing system 300, for example, scheduling execution of programs. Memory 320 may be or may include, for example, a Random Access Memory (RAM), a read-only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 320 may be or may include a plurality of possibly different memory units. Memory 320 may store for example, instructions to carry out a method (e.g., executable code 325), and/or data such as user responses, interruptions, etc.

Executable code 325 may be any executable code, e.g., an application, a program, a process, task, or script. Executable code 325 may be executed by controller 305 possibly under control of operating system 315. For example, execution of executable code 325 may cause the display or selection for display of medical images as described herein, and/or may implement any of the operations described herein. In some systems, more than one computing system 300 or components of computing system 300 may be used for multiple functions described herein. For the various modules and functions described herein, one or more computing systems 300 or components of computing system 300 may be used. Devices that include components similar or different to those included in the computing system 300 may be used and may be connected to a network and used as a system. One or more processor(s) 305 may be configured to carry out methods of the present disclosure by for example executing software or code. Storage 330 may be or may include, for example, a hard disk drive, a floppy disk drive, a Compact Disk (CD) drive, a CD-Recordable (CD-R) drive, a universal serial bus (USB) device or other suitable removable and/or fixed storage unit. Data such as instructions, code, medical images, image streams, etc. may be stored in storage 330 and may be loaded from storage 330 into memory 320 where it may be processed by controller 305. In some embodiments, some of the components shown in FIG. 3 may be omitted.

Input devices 335 may include for example a mouse, a keyboard, a touch screen or pad or any suitable input device. It will be recognized that any suitable number of input devices may be operatively coupled to computing system 300. Output devices 340 may include one or more monitors, screens, displays, speakers and/or any other suitable output devices. It will be recognized that any suitable number of output devices may be operatively coupled to computing system 300 as shown by block 340. Any applicable input/output (I/O) devices may be operatively coupled to computing system 300, for example, a wired or wireless network interface card (NIC), a modem, printer or facsimile machine, a universal serial bus (USB) device or external hard drive may be included in input devices 335 and/or output devices 340.

Multiple computer systems 300 including some or all of the components shown in FIG. 3 may be used with the described systems and methods. For example, a CE imaging device 212, a receiver, a cloud-based system, and/or a workstation or portable computing device for displaying images may include some or all of the components of the computer system of FIG. 3. A cloud platform (e.g., a remote server) including components such as computing system 300 of FIG. 3 may receive procedure data such as images and metadata, processes and generate a study, and may also display the generated study for the doctor's review (e.g., on a web browser executed on a workstation or portable computer). An "on-premises" option may use a workstation or local server of a medical facility to store, process and display images and/or a study.

Referring now to FIG. 4, there is shown a block diagram of an exemplary deep learning neural network 400 for classifying images. The deep learning neural network 400 can be implemented and executed by the computing system 300 of FIGS. 2 and 3. Generally, and as persons skilled in the art will understand, a deep learning neural network 400 includes an input layer, a plurality of hidden layers, and an output layer. The input layer, the hidden layers, and the output layer all include neurons or nodes. Certain neurons between the various layers are interconnected via weights, and such neurons in the deep learning neural network 400 compute an output value by applying a specific function to the input values coming from the neurons or nodes in the previous layer. The function that is applied to the input values is determined by a vector of weights and a bias. Learning, in the deep learning neural network, progresses by making iterative adjustments to these biases and weights. Certain layers may not be weighted layers and may be functional layers, such as max pooling layers, for example.

In various embodiments, a deep learning neural network 400 includes a convolutional neural network (CNN). In machine learning, a CNN is a class of artificial neural network that is most commonly applied to analyzing visual imagery. As persons skilled in the art will understand, the convolutional aspect of a CNN relates to applying matrix processing operations to localized portions of an image, and the results of those operations are sets of features that are used to train neural networks. A deep learning neural network 400 that includes a CNN typically includes convolution layers, activation function layers, and pooling (typically max pooling) layers to reduce dimensionality without losing too many features. Additional information may be included in the operations that generate these features. Providing unique information that yields features that give the neural networks information can be used to ultimately provide an aggregate way to differentiate between different data input to the neural networks.

In the illustrated embodiment, the deep learning neural network 400 may utilize one or more CNNs to classify one or more images 422 taken by the CE imaging device 212 (see FIG. 2) to a portion of the GIT. In the illustrated embodiment, the portions of the GIT classified by the deep learning neural network 400 include pre-small bowel 412, which includes the stomach, the small bowel 414, and the colon 416. The deep learning neural network 400 may be executed on the computer system 300 (FIG. 3). Persons skilled in the art will understand the deep learning neural network 400 and how to implement it.

The deep learning neural network 400 may be trained based on labels 424 for training images 422 and/or objects in training images. For example, an image 422 may be labeled as a portion of the GIT (for example, pre-small bowel, small bowel, or colon). In various embodiments, the training may include supervised learning. The training further may include augmenting the training images 422 to include adding noise, changing colors, hiding portions of the training images, scaling of the training images, rotating the training images, and/or stretching the training images. Persons skilled in the art will understand training of a deep learning neural network 400 and how to implement it.

In various embodiments, the deep learning neural network 400 may be used to classify images 422 captured by a capsule endoscopy imaging device 212 (see FIG. 2). The classification of the images 422 may include each image being classified to a segment of the GIT. For example, the image classifications may include the pre-small bowel 412, the small bowel 414, and the colon 416. The deep learning neural network 400 provides a classification score for each of the segments of the GIT. The classifications 412-416 of FIG. 4 are exemplary, and other classifications for other portions, segments, or consecutive segments of a GIT are contemplated to be within the scope of the present disclosure.

The description above relates to classifying images acquired by a capsule endoscopy device to segments of a GIT. The following detailed description will describe techniques for using classification scores to estimate points in an image stream corresponding to the capsule transitioning from one GIT segment to another GIT segment. Estimating such transitions are beneficial for organizing the stream of images from the capsule, which can include 50000 to 100000 images, and to reduce computing burden by isolating images associated with a particular segment of interest to a pathology study.

FIG. 5 shows an example of classification scores from a machine learning system, such as the deep learning neural network 400 of FIG. 4, for images of a gastrointestinal tract (GIT) acquired by a capsule endoscopy device. Each index value refers to an individual image, such that the graphs in FIG. 5 correspond to 50000 individual images of a GIT acquired by a capsule endoscopy device. The lower graph of FIG. 5 shows exemplary scores provided by the machine learning system (e.g., deep learning neural network 400) for classifying each image to a pre-small bowel portion of the GIT (e.g., the stomach and also out of body frames prior to swallowing) 412, a small bowel portion of the GU 414, and a colon portion of the GIT 416. The values and ranges of the scores are exemplary and can vary depending on the particular implementation of the machine learning system (e.g., deep learning neural network 400). In the illustrated embodiment, a high score (e.g., above a threshold) indicates a high confidence that the label of the frame is the one indicated by the score. For example, a high colon score indicates a high confidence of the frame being an image of the colon. In the case that scores are "intermediate," as defined by boundary thresholds, such intermediate scores would indicate moderate confidence and uncertainty. While the predicted classes and classification scores shown in FIG. 5 are presented across image frames, they may be treated as predicted classes and classification scores across time, as well. Accordingly, the classification scores and/or predicted classes may be treated as signals over time. As described later below in more detail, treating the classification scores or predicted classes as signals in time allows signal processing techniques to be applied to such signals.

The top graph of FIG. 5 illustrates an approach to classifying an image based on the classification scores, in which the predicted classification corresponds to the highest classification score. Using the deep learning neural network 400 of FIG. 4 as an example, in the top graph 510, a predicted class of "0" corresponds to pre-small bowel 412, a predicted class of "1" corresponds to small bowel 414, and a predicted class of "2" corresponds to colon 416. In the graphs 510, 520 of FIG. 5, it can be seen that a transition from pre-small bowel to small bowel occurs at approximately halfway between frames 0 and 5000, and a transition from small bowel to colon occurs at approximately halfway between frames 30000 and 35000. The top graph 510 indicates a true transition point 532 between small bowel and colon that is identified and marked by a medical expert examining the GIT images, and indicates a suggested transition point 534 based on the techniques of the present disclosure, which will be described below. As FIG. 5 illustrates, the suggested transition point 534 differs from the true transition 532 point by about 26.3 minutes. A reason for the difference is that the suggested transition point 534 may be a more conservative suggestion that has a lower chance of being a false positive. Because classification scores are often noisier and less clear than the example shown in FIG. 5, a more conservative suggestion increases the likelihood that images after the transition point are correctly classified.

In accordance with aspects of the present disclosure, FIG. 5 presents a transition detection operation whereby a suggested transition point 534 is identified when a predicted class changes in the correct direction and is maintained for a threshold number of frames or a threshold duration. The correct direction of predicted class change depends on the particular application. In the example of FIG. 5, the correct direction of predicted class change can be a change from "0" to "1" or "1" to "2." The threshold number of frames or threshold duration to maintain the predicted class can vary depending upon the particular application. In the example of FIG. 5, the threshold number of frames or threshold duration can correspond to a duration of about 26.2 minutes, but another threshold number of frames or duration can be used. In accordance with aspects of the present disclosure, the operation of FIG. 5 for suggesting a transition point may be referred to as a "simple" transition detection in view of the computational simplicity of identifying the suggested transition. Additionally, the computational simplicity permits the operation of FIG. 5 to be applied for both an online transition detection and an offline transition detection.

In various embodiments, when the "simple" transition detection is used in an online application, the detection can estimate the occurrence of a transition during the procedure and/or relatively shortly after the transition occurs (e.g., up to an hour, an hour and a half or up to two hours after the transition occurs). Based on the estimated occurrence of the transition, a message can be provided, e.g., to the patient, to indicate that the procedure has ended and a receiving device (e.g., 214, FIG. 2) can be unsecured or removed from the patient. Such a message would permit a patient to fully resume his/her activities without waiting for the capsule to exit the patient body.

Figure 6:
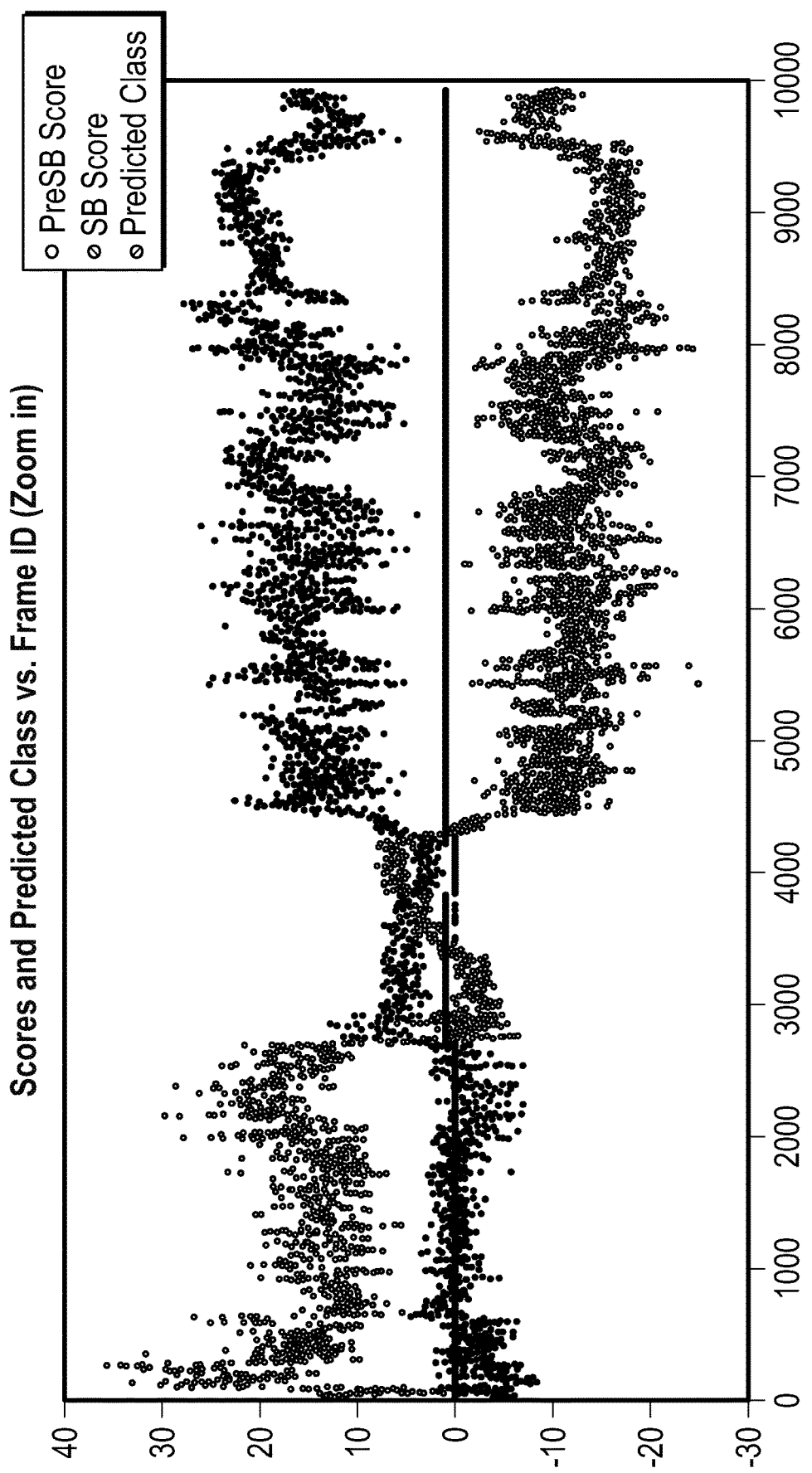
FIG. 6 is a graph enlarging a portion of the graph of FIG. 5.

The graph of FIG. 6 is an enlarged portion of FIG. 5 and illustrates a portion of the pre-small bowel scores and the small bowel scores for image indices 0 through 10000. Between approximately indices 2800 and 4200, the classification scores for pre-small bowel and for small bowel are more similar, and the classification corresponding to the highest score fluctuates back and forth. Therefore, a transition point within the index range of 2800 and 4200 may not have high confidence. The description below provides techniques for refining and improving confidence of transition points.

Figure 7:
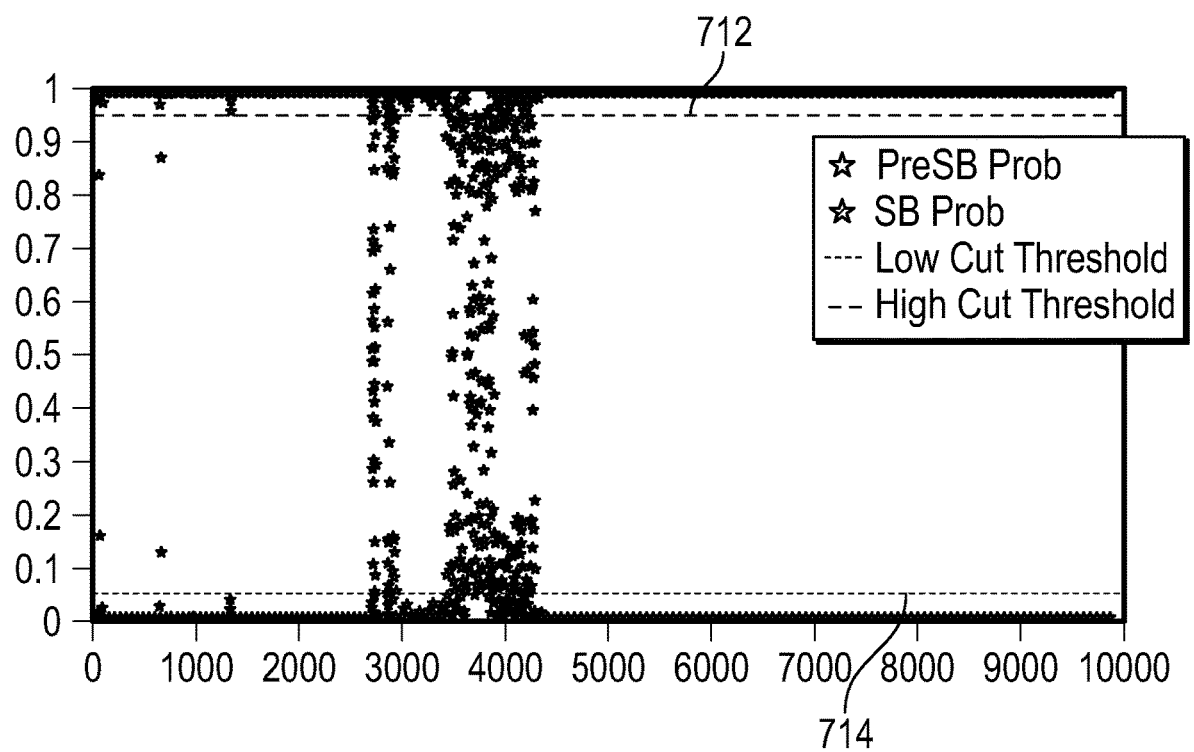
FIG. 7 is a graph of exemplary normalized scores for the classification scores of FIG. 6, in accordance with aspects of the disclosure.
Figure 8:
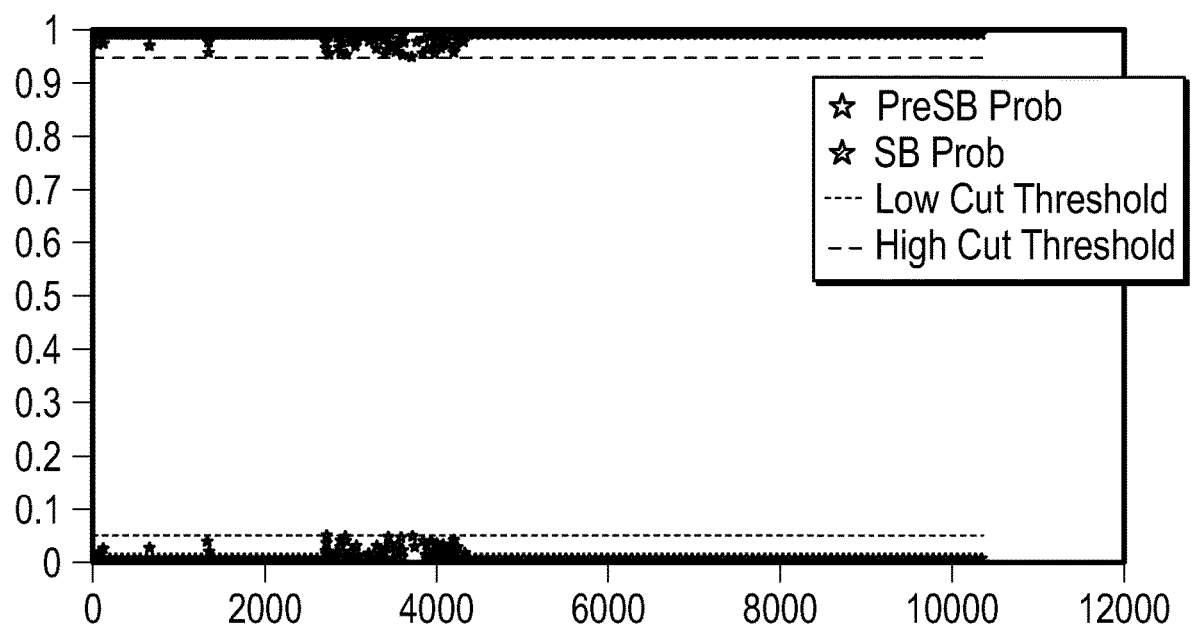
FIG. 8 is a graph of applying an exemplary confidence criterion to the normalized scores of FIG. 7, in accordance with aspects of the disclosure.

FIG. 7 is an example of a technique for removing classification scores which do not satisfy a confidence criterion and retaining classification scores which do satisfy the confidence criterion. In the illustrated embodiment, the classification scores are normalized to be between 0 and 1. In various embodiments, a different normalization can be used, and normalization can be linear or non-linear. The confidence criterion of FIG. 7 includes an upper threshold 712 and a lower threshold 714. Normalized scores which are between the upper threshold 712 and the lower threshold 714 would not meet the confidence criterion and are removed. Normalized scores which are above the upper threshold 712 or below the lower threshold 714 would meet the confidence criterion and are retained, as shown in FIG. 8. The result in FIG. 8 is a subset of images whose classification scores meet the confidence criterion. The classification scores of the subset of images may be treated as a signal over time. The confidence criterion illustrated in FIGS. 7 and 8 are exemplary, and other confidence criteria are contemplated to be within the scope of the present disclosure. For example, signal processing techniques for removing noise may be applied in addition to or in place of a confidence criterion.

Figure 9:
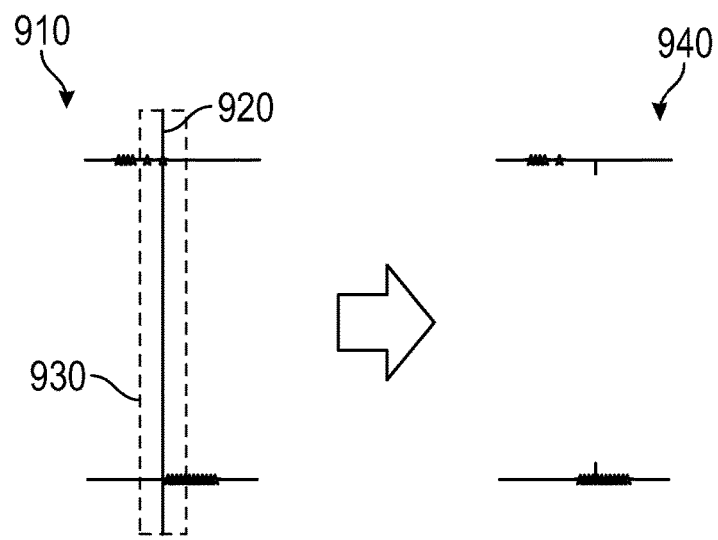
FIG. 9 is a graph of an exemplary smoothing operation, in accordance with aspects of the disclosure.

In various embodiments, the result in FIG. 8 may be further processed or may not be further processed. FIG. 9 is an example of further processing which may be performed and illustrates a smoothing operation. FIG. 9 is one example of processing for refining classifications by applying signal processing techniques to process a signal over time corresponding to the image classifications. The left-side graph 910 of FIG. 9 reflects a subset of images whose classifications fluctuate between two classes. In various embodiments, the smoothing processing operates to modify classifications to a more prevalent classification surrounding the classifications.

In accordance with aspects of the present disclosure, the smoothing operation can be applied to each image, such as image 920. In various embodiments, for each image, the smooth operation involves accessing the classifications of images within a window 930 around the image 920 and then refining the classification of the image 920 to a median of the classifications of the images within the window 930. An exemplary window 930 is illustrated in FIG. 9 and is centered at a particular image. The image centered in the window 930 has classification "1." However, as can be seen from FIG. 9, the median classification within the window 930 is classification "0." Therefore, the classification of the image 920 centered in the window 930 is refined/revised from classification "1" to classification "0," as shown by the right-side graph 940 in FIG. 9.

The illustrated effect of the smoothing operation is exemplary, and results of applying the smoothing operation will vary depending on the distribution of classifications and the size of the window. The size of the window can vary depending on the particular application that is being implemented. In various embodiments, the window need not be centered about an image and can be an entirely forward-extending window or an entirely backward-extending window or can be positioned about an image in another position. Such variations and other variations of the window are contemplated to be within the scope of the present disclosure. Additionally, smoothing operations other than a median computation are contemplated. For example, in various embodiments, the smoothing operation can involve a majority selection or a supermajority selection, or another operation. Such variations of a smoothing operation are contemplated to be within the scope of the present disclosure. Other processing for refining classifications are contemplated, including other signal processing techniques for processing a signal corresponding to image classifications.

Figure 10:
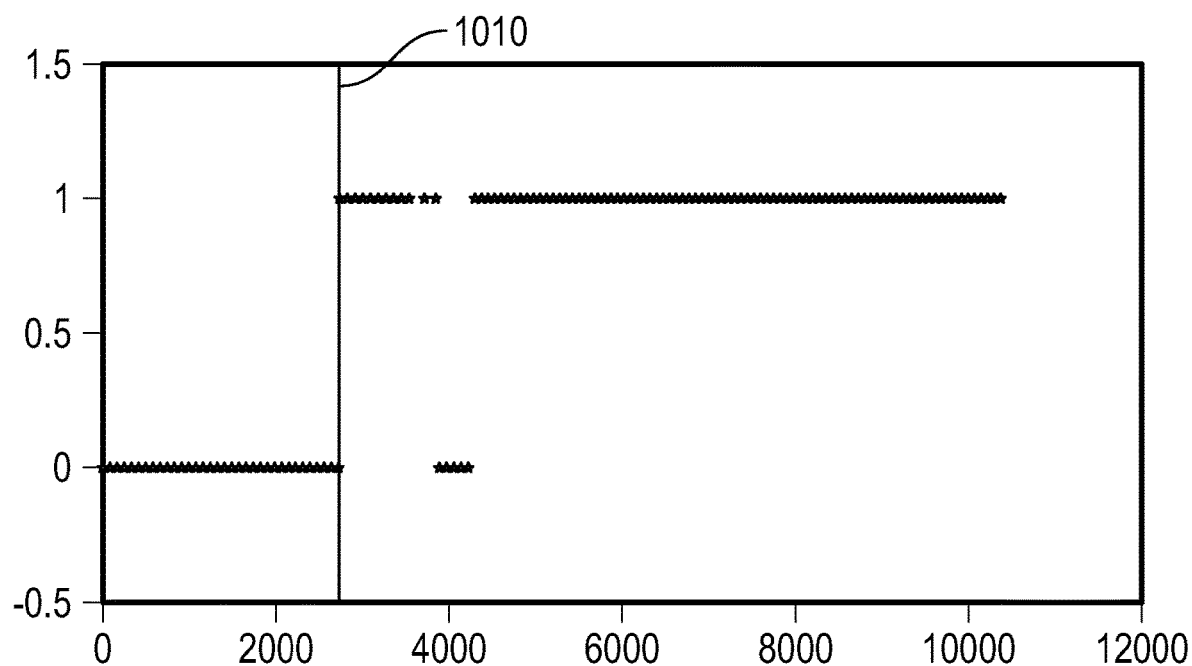
FIG. 10 is a graph of an exemplary estimated transition between two adjacent segments of a gastrointestinal tract, in accordance with aspects of the disclosure.

In various embodiments, a smoothing operation, such as in FIG. 9, can be used in conjunction with a confidence criterion filtering, such as in FIGS. 7 and 8. In various embodiments, a smoothing operation, such as in FIG. 9, can be used without using confidence criterion filtering. In the illustrated embodiments, image classifications corresponding to FIG. 8 are shown in FIG. 10. Applying a smoothing operation with a relatively narrow window to the classifications of FIG. 10 would not produce a noticeable or significant difference. Using the classifications in FIG. 10, a directional transition point 1010 from class "0" to class "1" is identified without applying a threshold delay (e.g., 26.2 minute delay of FIG. 5). If class "0" corresponds to classification of an image as pre-small bowel and class "1" corresponds to classification of an image as small bowel, then the transition 1010 would indicate a transition of the images from images of pre-small bowel, such as the stomach, to images of the small bowel. As another example, if class "0" corresponds to classification of an image as small bowel and class "1" corresponds to classification of an image as colon, then the transition 1010 would indicate a transition of the images from images of the small bowel to images of the colon. Although no threshold delay is applied in FIG. 10, it is contemplated that a delay as shown in FIG. 5 (e.g., 26.2 minutes) could be applied to the operation of FIG. 10 as well. Such a delay may not be needed, however, due to the refinements provided by the de-noising operation of FIGS. 7 and 8 and by the smoothing operation of FIG. 9. Such variations are contemplated to be within the scope of the present disclosure.

In various embodiments, and referring again to FIG. 7, the transition may be expressed as a range (not shown). In the example of FIG. 7, the transition may be indicated as occurring between approximately index 2800 and index 4200. A range-based transition may be beneficial in various situations. Using class "0" as pre-small bowel and class "1" as small bowel, for example, a range-based transition would indicate that images before index 2800 are most likely to be images of pre-small bowel, whereas images after index 4200 are most likely to be images of the small bowel. If images of the small bowel are desired, then images before index 2800 can be ignored, and if images of the pre-small bowel are desired, then images after index 4200 can be ignored. In both cases, however, images between index 2800 and index 4200 can be included as part of both image subsets.

The aspects and embodiments of FIGS. 7-10 described above are exemplary and variations are contemplated to be within the scope of the present disclosure. For example, FIGS. 9 and 10 show that certain frames around index 3500 are removed for not meeting a confidence criterion, thereby leaving gaps in classifications around index 3500. In various embodiments, the remaining images are re-indexed to be consecutive (not shown), such that there would be no gaps in FIG. 9. In such a case, the X-axis represent an index number and would not be an original frame number. Such variations and other variations are contemplated to be within the scope of the present application.

In contrast to the "simple" transition detection disclosed in connection with FIG. 5, the transition detection operations of FIGS. 7-10 may be referred to as "baseline" transition detection, which can include the confidence criterion/de-noising operation of FIGS. 7 and 8, the smoothing operation of FIG. 9, and the no-delay transition detection of FIG. 10.

Figure 11:
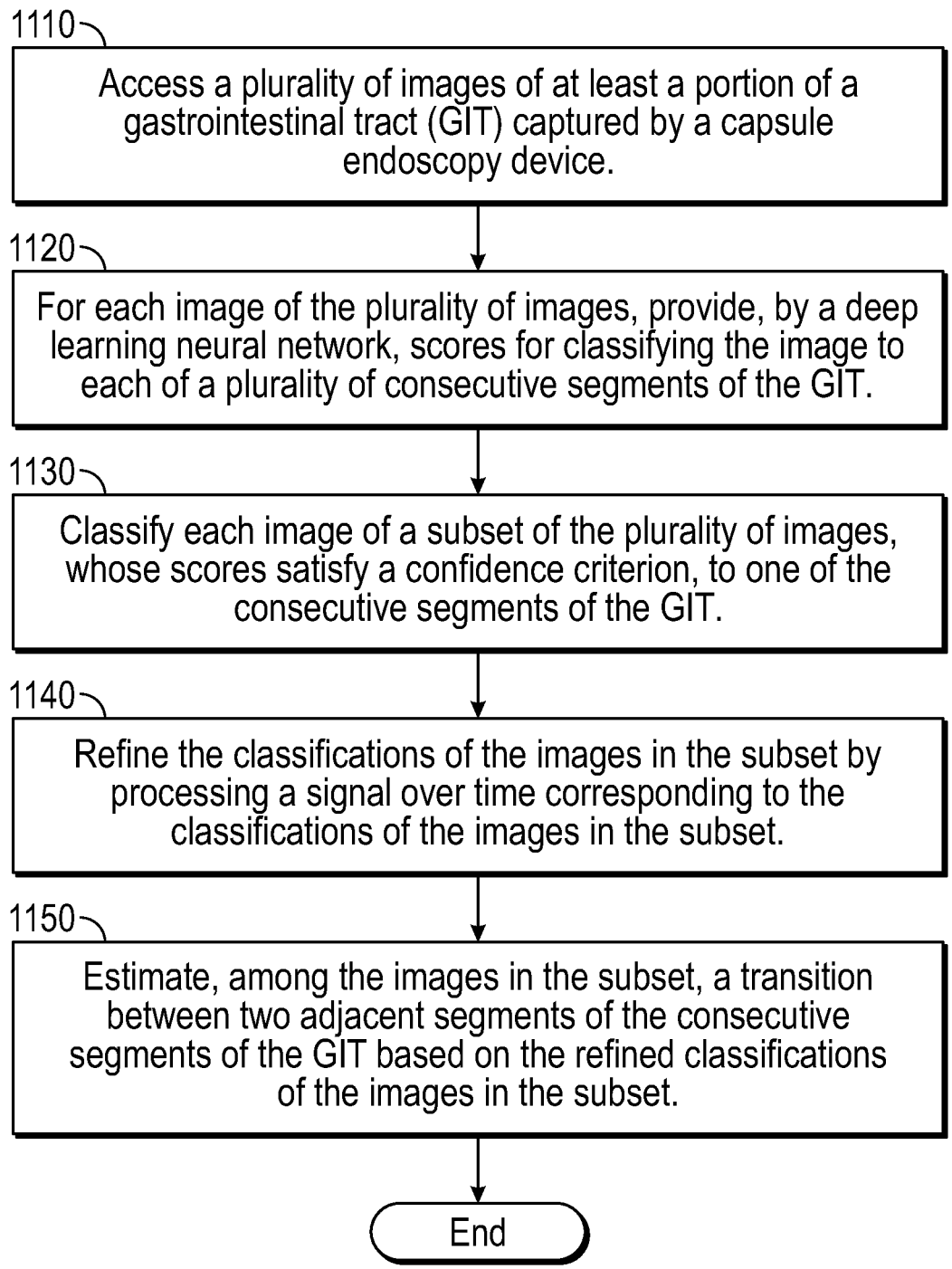
FIG. 11 is a flow diagram of an exemplary operation of estimating a transition between two adjacent segments of a gastrointestinal tract, in accordance with aspects of the disclosure.

Referring now to FIG. 11, there is shown a flow chart of an operation in accordance with FIGS. 4-10. At block 1110, the operation accesses a plurality of images of at least a portion of a gastrointestinal tract (GIT) captured by a capsule endoscopy device. At block 1120, for each image of the plurality of images, the operation provides, by a deep learning neural network, scores for classifying the image to each of a plurality of consecutive segments of the GIT. At block 1130, the operation classifies each image of a subset of the plurality of images, whose scores satisfy a confidence criterion, to one of the consecutive segments of the GIT. At block 1140, the operation refines the classifications of the images in the subset by processing a signal over time corresponding to the classifications of the images in the subset. And at block 1150, the operation estimates, among the images in the subset, a transition between two adjacent segments of the consecutive segments of the GU based on the refined classifications of the images in the subset.

The embodiments of FIGS. 4-11 are exemplary, and the disclosed systems and methods can be applied to segments of a gastrointestinal tract (GU) other than pre-small bowel, small bowel, and colon. Additionally, in various embodiments, another machine learning system can be applied in place of the deep learning neural network shown FIG. 4, such a classic machine learning system, a neural network with just two classes, or a neural network with more than three classes. As persons skilled in the art will understand, a "classic" machine learning system is one that involves feature engineering. Such applications are contemplated to be within the scope of the present disclosure.

The description above described an approach for estimating a transition between two adjacent segments of a GIT. The description below describes a technique for refining an estimated transition to an earlier point.

FIG. 12 is a block diagram of a deep learning neural network 1200 for classifying images to portions of a gastrointestinal tract (GIT). In the illustrated embodiment, the portions of the GIT classified by the deep learning neural network 1200 include pre-small bowel 1212, which includes the stomach, the small bowel 1214, and an anatomical feature 1216 adjacent to the transition point between the pre-small bowel 1212 and the small bowel 1214. Generally, the deep learning neural network 1200 of FIG. 12 can be used to classify images to a first segment of a GU, a second consecutive segment of the GU, and an anatomical feature adjacent to the transition point between the first segment and the second segment of the GIT. In the case of a transition from pre-small bowel to small bowel, the anatomical features adjacent to the transition point include a pyloric valve and a bulb. As explained below, such anatomical features can be used in identifying the transition point between the first and second segments of the GU in a stream of images.

By training the deep learning neural network 1200 to classify an anatomical feature adjacent to the transition point between two consecutive segments of a GIT, the illustrated deep learning neural network 1200 can be applied to refine an estimated baseline transition between the first and second segments as estimated by the approach of FIGS. 4-11. The deep learning neural network 1200 may be trained based on labels 1224 for training images 1222 and/or objects in training images. For example, an image 1222 may be labeled as pre-small bowel, anatomical feature, or small bowel. The deep learning neural network 1200 may be executed on the computer system 300 (FIG. 3). Persons skilled in the art will understand the deep learning neural network 1200 and how to implement it.

FIG. 13 is an example comparing classifications based on the deep learning neural network 400 of FIG. 4 and classifications based on the deep learning neural network 1200 of FIG. 12. The top graph 1310 of FIG. 13 shows classifications of images to pre-small bowel (class "0"), small bowel (class "1"), and colon (class "2"), and indicates an estimated transition 1340 between pre-small bowel and the small bowel, based on the approach described in connection with FIGS. 4-11. The middle graph 1320 shows classification of the same images to pre-small bowel (class "0"), entrance to small bowel (class "1"), and small bowel (class "2"), based on classification scores provided by the deep learning neural network 1200 of FIG. 12. The estimated transition 1340 between pre-small bowel and small bowel is placed at the same location in the top graph 1310 and the middle graph

1320. The entrance to small bowel includes a bulb structure (i.e., the duodenal bulb), which can be the anatomical feature adjacent to the transition point between the stomach and the small bowel. Since the duodenal bulb is located at the beginning of the SB, it can be a better fiducial for identifying the transition than other anatomical features, such as the pyloric valve or pylorus, which are part of the stomach. Furthermore, the duodenal bulb has a unique structure, which facilitates its detection. Its mucosa appears different from other types of mucosa in the GIT. It does not include villi or folds, and the bulb is open. For convenience, the term "entrance to small bowel" may be used to describe such anatomical feature. However, it will be understood that the actual classification is an anatomical feature adjacent to the transition point between the two GIT segments.

The bottom graph 1330 is an enlarged version of a portion of the middle graph 1320 around the estimated transition 1340 between pre-small bowel and small bowel. As shown by the bottom graph 1330, the classification of an entrance to the small bowel provides more context about where the estimated transition 1340 between pre-small bowel and small bowel is located relative to the images classified as entrance to the small bowel. As shown by the bottom graph 1330, the transition from pre-small bowel to small bowel may be earlier than the estimated transition 1340 in the top graph 1310, as images prior to the estimated transition 1340 point are classified as entrance to the small bowel.

In accordance with aspects of the present disclosure, the classification scores provided by the deep learning neural network 1200 of FIG. 12 can be used to refine an estimated baseline transition to an earlier point before the estimated baseline transition. FIG. 14 shows a graph of a computation that is based on the pre-small bowel classification score 1212 and the entrance to small bowel score 1216 of FIG. 12, for images in the vicinity of the estimated transition 1340. The value in the graph at each index is a cumulative sum. In particular, for an index k, the cumulative sum $S_k$ is provided by:

$$S_k = \Sigma_{i=1}^{k}(\text{Score}_i^{class\_1} - \text{Score}_i^{class\_0}),$$

where $\text{Score}_i^{class\_1}$ is the class "1" score for index i and $\text{Score}_i^{class\_0}$ is the class "0" score for index i.

Because the class "1" score will be less than the class "0" score for the initial images, the value of $S_k$ will be negative for the initial images. For example, when class "0" corresponds to pre-small bowel and class "1" corresponds to entrance to small bowel, the pre-small bowel score will be greater for the initial images because the initial images are images of pre-small bowel. As long as the images are images of pre-small bowel, the values of $S_k$ will decrease, such as in region 1410. Once the images are images of entrance to the small bowel, however, the entrance to small bowel score becomes greater, and the values of $S_k$ will increase, such as in region 1420. As shown in FIG. 13, however, the classifications between pre-small bowel and entrance to small bowel can fluctuate, and this is shown by the graph of FIG. 14 fluctuating in regions 1410 and 1420. However, once the images are images of entrance to the small bowel, classifications of entrance to the small bowel will be more frequent, and the values of $S_k$ will increase more often than decrease. Therefore, generally, a trend of decreasing values of $S_k$ can indicate classification to the pre-small bowel, and a trend of increasing values $S_k$ can be indicative of classification to the entrance to the small bowel. The transition, then, would be suggested by a true or global minimum 1430 in the value of $S_k$ that occurs before the originally estimated baseline transition 1340. Persons skilled in the art will recognize various techniques for determining a true minimum within a range of values.

The cumulative sum $S_k$ described above is exemplary and variations are contemplated. For example, in various embodiments, the cumulative sum $S_k$ can increase prior to a transition point and decrease after the transition point, such that the graph of FIG. 14 would be inverted, and the transition would correspond to a true or global maximum rather than a true minimum. Additionally, the technique of FIG. 14 can be applied to consecutive segments of a GIT other than pre-small bowel and small bowel. Generally, the technique includes, for each image of a plurality of images: (i) computing a difference between the score for classifying the image to the first segment of the GIT and the score for classifying the image to the entrance of the second segment of the GU, and (ii) computing a sum of the computed differences from a first image of the plurality of images through the image. Then, the refined transition is an image corresponding to a global minimum or maximum in the computed sums prior to the originally estimated baseline transition.

Accordingly, FIGS. 12-14 describe an operation of refining an estimated baseline transition to an earlier point before the estimated baseline transition. An operation of refining an estimated baseline transition to a later point after the estimated baseline transition is described in connection with FIG. 15.

FIG. 15 shows a graph of classification scores for a first segment of two adjacent segments of a GIT, and indicates an estimated baseline transition 1510 from the first segment to the second segment of the two adjacent segments of the GU. For example, the first segment can be a small bowel and the second segment can be a colon. The estimated baseline transition 1510 can be determined based on the techniques described in connection with FIGS. 4-11.

In accordance with aspects of the present disclosure, if the classification scores for the first segment increase above a threshold value 1520 for at least a burst duration 1530, after the estimated transition 1510, then the bursts of classification to the first segment can be used to refine the estimated transition 1510 to a later point after the bursts. The threshold value 1520 and the burst duration 1530 can vary based on the particular application and the particular portions of the GIT of interest. As an example, the estimated baseline transition 1510 may be a transition from small bowel to colon. If, after the estimated transition 1510 to the colon, classification scores for the small bowel increase above a threshold value 1520 for at least a burst duration 1530, then such bursts of classification to the small bowel can be used to refine the estimated transition 1510 to a later point after the bursts. Such bursts of classification to the small bowel can indicate, for example, that fecal material from the colon was introduced to the final portions of the small bowel, thereby causing the final portions of the small bowel to initially be misclassified as the colon. The bursts can be used to potentially recognize this situation and to move the estimated baseline transition 1510 to a later point that is potentially closer to a true transition from small bowel to colon.

Variations of the technique of FIG. 15 are contemplated. For example, in various embodiments, rather than a burst, if classifications after the estimated transition fluctuate between two classifications in a manner that exceeds a fluctuation tolerance, the estimated transition can be refined to a later point after the estimated transition. Other variations are contemplated to be within the scope of the present disclosure.

Accordingly, the above described systems and methods for analyzing a stream of in-vivo images of a gastrointestinal tract captured by a capsule endoscopy device, to perform transition detection in the stream of in-vivo images. Certain transition detection operations can be used in an offline application, and certain transition detection operations can be used in an online application.

As a first example of an offline application, a classification machine learning system with at least two classes is used, such as two classes corresponding to an earlier segment of the GIT and a later segment of the GIT (e.g., pre-small bowel and small bowel). This machine learning system may be a classic machine learning system or a deep learning neural network (e.g., FIG. 4). The classification scores provided by the machine learning system are treated as a signal over time. A noise filtering signal processing operation can be performed (e.g., FIGS. 7 and 8). Alternatively, or in addition, a smoothing signal processing operation can be performed (e.g., FIG. 9). A change in the resulting signal from an earlier segment to a later segment of the GIT can be identified as an estimated transition, such as an estimated transition from pre-small bowel to small bowel, or an estimated transition from small bowel to colon.

As a second example of an offline application, a first classification neural network with at least two classes can be used (e.g., pre-small bowel and small bowel), and a second classification neural network can be used which also classifies an anatomical structure or region adjacent to the transition between the different anatomical sections (e.g., the end of small bowel or beginning of colon). Examples of the anatomical structures include a pyloric valve at the end of the stomach or a bulb structure at an entrance to the small bowel. In various embodiments, other machine learning systems can be used in place of a classification neural network, such as a classic machine learning system.

As a third example of an offline application, a classification machine learning system with at least three classes is used, such as three classes corresponding to three consecutive segments of a GIT (e.g., FIG. 4: pre-small bowel, small bowel, and colon). A first transition from pre-small bowel to small bowel can be detected in the manner described herein (e.g., FIGS. 7-10, 12-14), and a second transition from small bowel to colon can be detected in the manner described herein (e.g., FIGS. 7-10, 15).

As an example of an online application, the "simple" transition detection operations of FIG. 5 can be used to estimate occurrence of a transition from an earlier segment to a later segment of the GIT (e.g., from stomach to small bowel, or from small bowel to colon). A message can be provided based on the detected occurrence to inform the patient that the procedure has ended and that a receiving device (e.g., 214, FIG. 2) can be removed. Such an online application may shorten and ease the procedure for the patient and permits the patient to fully resume his/her daily activities before the capsule exits the body.

An application that may involve both online and offline aspects. As an example, a classification neural network with at least two classes (e.g., FIG. 4: small bowel and colon) can be applied in an online manner (e.g., FIG. 5) to determine a transition point (e.g., from small bowel to colon). Additionally, signal processing techniques (e.g., FIGS. 7-10, 12-15) can be applied in an offline manner to refine the online transition point.

Another example of an application having both online and offline aspects includes GIT segmentation with online transition detection (e.g., FIG. 5) and offline refinement of the online transition point (e.g., FIGS. 7-10, 12-15).

Even though examples are shown and described with respect to images captured in vivo by a capsule endoscopy device, the disclosed technology can be applied to images captured by other devices or mechanisms, including anatomical images captured by MRI or images captured with infrared instead of or in addition to visible light, for example. As another example, the disclosed technology can be applied to online detection of transitions during various procedures, such as online detection of pre-small bowel to small bowel transition during an endoscopy procedure, or to online detection of colon to small bowel transition during a colonoscopy.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in various embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)."

Any of the herein described operations, methods, programs, algorithms, or codes may be converted to, or expressed in, a programming language or computer program embodied on a computer or machine readable medium. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, Python, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

It should be understood that the foregoing description is only illustrative of the present disclosure. To the extent consistent, any or all of the aspects detailed herein may be used in conjunction with any or all of the other aspects detailed herein. Various alternatives and modifications can be devised by those skilled in the art without departing from the disclosure. Accordingly, the present disclosure is intended to embrace all such alternatives, modifications, and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for analyzing images, comprising:
at least one processor; and
at least one memory storing instructions which, when executed by the at least one processor, cause the system to:
access a plurality of images of at least a portion of a gastrointestinal tract (GIT) captured by a capsule endoscopy device;
for each image of the plurality of images, provide, by a deep learning neural network, scores for classifying the image to each of a plurality of consecutive segments of the GIT;
classify each image of a subset of the plurality of images, whose scores satisfy a confidence criterion, to one of the consecutive segments of the GIT;
refine the classifications of the images in the subset by processing a signal over time corresponding to the classifications of the images in the subset; and
estimate, among the images in the subset, a transition between two adjacent segments of the consecutive segments of the GIT based on the refined classifications of the images in the subset.

2. The system according to claim 1, wherein the instructions, when executed by the at least one processor, further cause the system to provide the subset of the plurality of images as images from the plurality of images whose scores, when normalized, are above an upper threshold or below a lower threshold but are not between the upper threshold and the lower threshold.

3. The system according to claim 2, wherein in refining the classifications of the images in the subset, the instructions, when executed by the at least one processor, cause the system to apply a smoothing operation to the classifications of the images in the subset to provide the refined classifications of the images in the subset.

4. The system according to claim 3, wherein in applying the smoothing operation, the instructions, when executed by the at least one processor, cause the system to, for each image in the subset:
access the classifications of images within a window around the image; and
select, as the refined classification of the image, a median of the classifications of the images within the window.

5. The system according to claim 1, wherein the transition between the two adjacent segments is a transition between an earlier segment of the GIT and a later segment of the GIT.

6. The system according to claim 5, wherein the two adjacent segments are the stomach and the small bowel, wherein the instructions, when executed by the at least one processor, further cause the system to determine a presence or an absence of a stomach retention condition based on comparing the scores for the plurality of images to a threshold number of small bowel classifications.

7. The system according to claim 1, wherein the two adjacent segments include a first segment of the GIT and a second segment of the GIT,
wherein the instructions, when executed by the at least one processor, further cause the system to:
for each image of the plurality of images, provide, by a second deep learning neural network, scores for classifying the image to the first segment of the GIT, the second segment of the GIT, and an anatomical feature adjacent to a transition point between the first segment and the second segment; and
refine the transition between the first segment and the second segment of the GIT to an earlier point before the estimated transition based on the scores provided by the second deep learning neural network.

8. The system according to claim 7, wherein in refining the transition, the instructions, when executed by the at least one processor, cause the system to:
for each image of the plurality of images:
compute a difference between the score for classifying the image to the first segment of the GIT and the score for classifying the image to the anatomical feature adjacent to the transition point between the first segment and the second segment of the GIT, and
compute a sum of the computed differences from a first image of the plurality of images through the image; and
determine the refined transition to be an image corresponding to a global minimum or maximum in the computed sums prior to the originally estimated transition.

9. The system according to claim 1, wherein the two adjacent segments include a first segment of the GIT and a second segment of the GIT,
wherein the instructions, when executed by the at least one processor, further cause the system to refine the transition between the first segment and the second segment to a later point after the estimated transition based on at least one of: bursts of classification to the first segment of GIT after the estimated transition, or fluctuation between classification to the first segment of the GIT and classification to the second segment of the GIT, beyond a fluctuation tolerance, after the estimated transition.

10. A system for analyzing images, comprising:
at least one processor; and
at least one memory storing instructions which, when executed by the at least one processor, cause the system to:
access a plurality of images of at least a portion of a gastrointestinal tract (GIT) captured by a capsule endoscopy device;
estimate, among the plurality of images, a transition between a first segment and a second segment of the GIT based on classification scores from a first deep learning neural network which classifies an image to at least two classifications, the at least two classifications including the first segment of the GIT and the second segment of the GIT; and
refine the transition between the first segment and the second segment of the GIT to an earlier point before the estimated transition based on classification scores for the plurality of images from a second deep learning neural network which classifies an image to at least three classifications, the at least three classifications including the first segment of the GIT, the second segment of the GIT, and an anatomical feature adjacent to a transition point between the first segment and the second segment of the GIT.

11. The system according to claim 10, wherein in refining the transition, the instructions, when executed by the at least one processor, cause the system to:
for each image of the plurality of images:
compute a difference between the score for classifying the image to the first segment of the GIT and the score for classifying the image to the anatomical feature adjacent to the transition point between the first segment and the second segment of the GIT, and
compute a sum of the computed differences from a first image of the plurality of images through the image; and
determine the refined transition to be an image corresponding to a global minimum or maximum in the computed sums prior to the originally estimated transition.

12. The system according to claim 10, wherein the first segment of the GIT is pre-small bowel, the second segment of the GIT is small bowel, and the anatomical feature adjacent to the transition point between the first segment and the second segment of the GIT is a bulb anatomical structure.

13. A system for analyzing images, comprising:
at least one processor; and
at least one memory storing instructions which, when executed by the at least one processor, cause the system to:
access a plurality of images of at least a portion of a gastrointestinal tract (GIT) captured by a capsule endoscopy device;
for each image of the plurality of images, provide, by a machine learning system, scores for classifying the image to each of at least two consecutive segments of the GIT;
perform noise filtering on the classification scores to provide remaining classification scores, the remaining classification scores corresponding to a subset of the plurality of images;
classify each image of the subset based on the remaining classification scores to provide a signal corresponding to the classifications; and
estimate a transition from an earlier segment to a later segment of the at least two consecutive segments of the GIT based on the classification signal.

14. The system according to claim 13, wherein the transition is a transition from pre-small bowel to small bowel, wherein the instructions are executed in an offline configuration after the capsule endoscopy device has exited a patient.

15. The system according to claim 14, wherein the instructions, when executed by the at least one processor, further cause the system to refine the transition to an earlier transition point corresponding to a global minimum of a function, the function based on cumulative sum of differences between classification scores corresponding to the pre-small bowel and classification scores corresponding to an anatomical feature adjacent to a transition point between the pre-small bowel and the small bowel.

16. The system according to claim 13, wherein the transition is a transition from small bowel to colon, wherein the instructions are executed in an offline configuration after the capsule endoscopy device has exited a patient.

17. The system according to claim 16, wherein the instructions, when executed by the at least one processor, further cause the system to refine the transition to a later transition point based on at least one of: bursts of classification to the small bowel after the transition, or fluctuation between classification to the small bowel and classification to the colon, beyond a fluctuation tolerance, after the transition.

18. The system according to claim 13, wherein the instructions, when executed by the at least one processor, further cause the system to remove non-relevant images including at least one of: images occurring before the transition or images occurring after the transition.

19. The system according to claim 13, wherein the instructions, when executed by the at least one processor, further cause the system to provide localization information to a user, the localization information including at least one of: information indicating that images before the transition are classified as images of the earlier segment of the GIT, or information indicating that images after the transition are classified as images of the later segment of the GIT.

20. The system according to claim 13, wherein the machine learning system provides scores for classifying images to each of at least three consecutive segments of the GIT, wherein the transition is a transition from a first segment to a second segment of the at least three consecutive segments of the GIT,
wherein the instructions, when executed by the at least one processor, further cause the system to estimate a second transition from the second segment to a third segment of the at least three consecutive segments of the GIT based on the classification signal.

* * * * *